United States Patent
Hansraj et al.

(10) Patent No.: US 11,896,510 B2
(45) Date of Patent: Feb. 13, 2024

(54) SPINE FORCE MODULATING ASSEMBLY

(71) Applicants: Kenneth K. Hansraj, Congers, NY (US); Jonathan A. Hansraj, Congers, NY (US); Marcia D. Griffin Hansraj, Congers, NY (US); Uros Rozic, Ljubljana (SI)

(72) Inventors: Kenneth K. Hansraj, Congers, NY (US); Jonathan A. Hansraj, Congers, NY (US); Marcia D. Griffin Hansraj, Congers, NY (US); Uros Rozic, Ljubljana (SI)

(*) Notice: Subject to any disclaimer, the term of this patent is extended or adjusted under 35 U.S.C. 154(b) by 0 days.

(21) Appl. No.: 18/084,483

(22) Filed: Dec. 19, 2022

(65) Prior Publication Data
US 2023/0190507 A1    Jun. 22, 2023

Related U.S. Application Data

(60) Provisional application No. 63/291,384, filed on Dec. 18, 2021.

(51) Int. Cl.
*A61F 5/02* (2006.01)
(52) U.S. Cl.
CPC .................................... *A61F 5/028* (2013.01)
(58) Field of Classification Search
CPC .......... A61F 5/028; A61F 5/026; A61F 5/024; A61F 5/022; A61F 5/02; A61F 2007/0024; A61F 2007/0025; A61F 2007/0026; A61F 2007/0027
See application file for complete search history.

(56) References Cited

U.S. PATENT DOCUMENTS

| | | | | |
|---|---|---|---|---|
| 4,820,221 A | * | 4/1989 | Aubrey | A61F 5/02 441/106 |
| 2016/0038330 A1 | * | 2/2016 | Kim | A61F 5/026 602/19 |
| 2020/0188159 A1 | * | 6/2020 | Hatch | A61F 5/028 |

FOREIGN PATENT DOCUMENTS

| | | | | |
|---|---|---|---|---|
| CN | 108601666 A | * | 9/2018 | A61F 5/026 |
| EP | 3804665 A1 | * | 4/2021 | A61F 5/02 |
| ES | 2498271 T3 | * | 9/2014 | A61F 5/026 |
| JP | 2012152366 A | * | 8/2012 | |
| KR | 20190133607 A | * | 12/2019 | |
| KR | 102118778 B1 | * | 6/2020 | |
| KR | 102402876 B1 | * | 5/2022 | |

* cited by examiner

*Primary Examiner* — Tarla R Patel
(74) *Attorney, Agent, or Firm* — Barry Choobin; Patent 360

(57) ABSTRACT

A spine force modulating assembly for supporting a human spine that prevents, slows down, and or treats spine-related disorders. The spine force modulating assembly includes a frame of a length proportional to a distance between a third thoracic spine bone and a first sacral spine bone of a spine of a wearer of the spine force modulating assembly. The frame is of a "S" shape and configured to support a spine portion between the third thoracic spine bone and the first sacral spine bone. The spine force modulating assembly further includes a pair of shoulder straps extending from near the upper end of the frame and a pair of waist straps extending from near the lower end of the frame.

14 Claims, 9 Drawing Sheets

SPINE FORCE MODULATING ASSEMBLY

CROSS-REFERENCE TO RELATED APPLICATIONS

This application claims priority from the U.S. provisional patent application Ser. No. 63/291,384, filed on Dec. 18, 2021, which is incorporated herein by reference in its entirety.

FIELD OF INVENTION

The present invention relates to a spine force modulating assembly, and more particularly, the present invention relates to a novel dynamic, anatomic, postural, conforming spine force modulating assembly.

BACKGROUND

Back pain, neck pain, sciatica, and arm pain are the most common medical complaints around the globe. It has been estimated that about 7% of the world's population is affected by back problems that have become a leading cause of disability worldwide. Neck pain affects about 4% of the global population and 11% of the population suffers with both neck pain and back pain.

A spinal column of an adult human consists of a cervical spine with a cervical lordosis shape, thoracic spine with a thoracic kyphosis shape, a lumbar spine with a lumbar lordosis shape, and the sacrum and the coccyx with a kyphosis shape. The cervical lordosis is the natural C-shape of the neck which is belly shaped. There are seven cervical vertebrae called the neck. The cervical spine is the neck. Normal cervical lordosis is 20 to 40 degrees. Thoracic kyphosis is the natural reverse C-shape of the mid-back spine which is reverse belly shaped. There are twelve thoracic vertebrae called the midback. Normal thoracic kyphosis is 20 to 40 degrees. Less than 20 degrees of kyphosis presents a hypokyphosis problem, while greater than 50 degrees presents a hyperkyphotic problem. The alignment of the thoracic spine is sensitive for forces placed onto the spine. Lumbar lordosis is the natural C-shape of the lower back which has a belly shaped curvature. The lumbar spine is the lower back consisting of 5 lumbar vertebrae. Normal lumbar lordosis is typically between 20 to 40 degrees. When the angle of the lumbar curve is large, often called a sway back, it can cause a lot of problems—including misalignment leading to pain. When the angle of the lumbar spine is too low a condition called flat back exists and may be associated with disc degeneration or herniated discs, causing pain.

The pathophysiology of both back and neck pains is well known. There are many causes for back pain and neck pain. Bodily injuries due to accident, muscle strain, lifting of weights in day-to-day life are known causes of pain. Occupation factors can also result in many kinds of pains. Bad postures of the body during rest, sleeping, working, and moving can also result in bodily pains. People working on laptops for about eight or more hours a day often report back pain and neck pain. Obesity is also a common cause of back and neck pains. The alignment of the cervical, thoracic and lumbar spines is sensitive to forces placed onto the spine.

The process of degeneration of the human intervertebral disc can be defined as crack propagation of the disc space, degenerative disc disease, herniation of an intervertebral disc, and spinal stenosis. Crack propagation of the disc space: Every time a person bends, lifts, twists, or reaches, the person exerts spinal forces onto the intervertebral disc. Exertion of these forces may lead to cracking of the disc spaces, a process called degenerative disc disease. Degenerative disc disease describes the wear and tear of the disc. Degenerative disc disease is a misnomer because it sounds like a progressive and threatening condition. This process occurs naturally with age. However, it is not strictly degenerative and is not actually a disease. Degenerative disc disease can also be accelerated by a motor vehicle accident or labor and other repetitive activities, known as traumatic degeneration. With bending, lifting, twisting, or reaching the disc interface sees mechanical stress. This stress can result into an annular tear, which is a tear of the disc space. With increased stress, more wear and tear are seen by the annulus of the discs causing more annular tears. With wear and tear, the annulus may exude inflammatory chemicals which are caustic and painful to the surrounding tissues and nerves. With additional wear and tear, then the inner nucleus may propagate through the annulus fibrosus. Herniation of an intervertebral disc happens when the inner nucleus pulposus travels through the annulus fibrosus. The extruded inner nucleus can now press on the spinal cord and nerve roots, causing pain, weakness, and numbness. Spinal stenosis occurs with time, age, and calcification, when bony bits of osteophytes form, blocking the central channel in a process called central stenosis, or blocking the nerve channels, called neural foraminal stenosis.

While wear, tear, and break down of the discs is natural and unavoidable, certain factors accelerates the process. Repetitive bending, lifting, twisting, reaching, vibration exposure, poor posture, poor body mechanics, weak abdominal and extensor muscles, smoking, and obesity can increase the rate of disc break-down. Preventative measures such as exercises and orthopedic back supports are prescribed to limit or slow down the wear and tear process. For example, a U.S. patent Ser. No. 10/517,749 teaches that an orthopedic brace which includes a pair of back panels, a pair of front panels, and a closure system, that a lateral end of each front panel is releasably couplable to a lateral end of each back panel at a desired angle. A ventral end of each front panel includes an attachment provision configured to allow one of the front panels to releasably attach to the other of the front panels generally over an abdomen of a wearer. However, the said brace only supports the lumbar spine. Another U.S. Pat. No. 9,393,149 describes a double pull body brace that also support only the lumbar spine.

Thus, the known orthopedic back support articles suffer from one or more limitations and drawbacks. The major limitation is that most of the orthopedic back support articles are designed to support the lumbar spine only. Moreover, the orthopedic back support articles provide a general support which may or may not be effective. A need is therefore appreciated for a novel dynamic, anatomic, postural, conforming spine force modulating assembly which reliably measures, absorbs, and subsumes the forces seen by the spine.

Different forces on the spine in day-to-day life were studied using five finite element studies. The study was used to design and develop the disclosed assembly. The following assessment was made using the finite element analysis: estimating the forces and magnifications seen by the spine when bending the head forward called text neck; the forces seen by the spine when an item is lifted; the forces seen by the spine when an item is placed into a backpack; the forces displayed to the spine with belly fat present by waist circumference; and the breast forces placed upon the spine by commercial bra sizes.

Finite Element Analysis Described: Proper alignment of the cervical spine is very sensitive for forces placed onto the spine. In a study "Assessment of stresses in the cervical spine caused by posture and position of the head" it was found that: the head weighs 10 to 12 pounds to the neck in a neutral position; when flexed forward at 15 degrees, the head exerts 27 pounds of force; when flexed forward at 30 degrees, the head exerts 40 pounds of force; when flexed forward at 45 degrees, the head exerts 49 pounds of force; when flexed forward at 60 degrees, the head exerts 60 pounds of force. Lifting finite mathematical studies say that when the person lifts an item: close to the body then the spine force is half the weight of the item; 45 degrees from the body then the spine force is 2× the weight; 90 degrees from the body then the spine force is 4× the weight of the item. A regular person lifts 20 to 50 pounds per day. At work, whatever someone lifts in a day, he/she does 5 days a week, for 50 weeks per year therefore 250 times per year. Everyday people, including those who work from home, lift daily items. It is estimated that the average person lifts 5,000 to 18,000 pounds a year, in their daily living.

It was estimated for regular persons carrying 5,000 pounds of weight per year in their hands: when the regular person lifts items close to the body then the spine force is half the weight of the item, or 2,500 pounds of force to the spine, per year; when 45° from the body then the spine force is 2× the weight i.e., 10,000 pounds of force to the spine, per year; and when 90° from the body then the spine force is 4× the weight of the item i.e., 20,000 pounds of force to the spine, per year It was estimated for a regular person lifting at 18,000 pounds per year that when a regular person carries 18,000 pounds of weight per year in their hands: close to the body then the spine force is half the weight of the item i.e., 9,000 pounds of force to the spine, per year; when 45° from the body then the spine force is 2× the weight, the force is 36,000 pounds of force to the spine, per year; when 90° from the body then the spine force is 4× the weight of the item i.e., 72,000 pounds of force to the spine, per year.

For People who lift all day because of occupation, it was estimated that when delivery workers lift 1,000 pounds per day, it amounts to 250,000 pounds per year; when they lift 4,000 pounds per day, this is 1,000,000 pounds per year; and when they lift 6,000 pounds per day, this is 1.5 million pounds per year. When the delivery person lifts 1,000,000 pounds of items close to the body then the spine sees force that is half the weight, or 500,000 pounds of force, per year; when 45° away from the body than the spine experiences force two times the weight, or 2,000,000 pounds of force, per year; and when 90° away from the body, the spine sees forces four times the weight, or 4,000,000 pounds of force, per year.

In the study, it was further estimated that lifting 5 gallons of water is 40 pounds of weight. Water delivery people may lift 100 bottles or 4,000 pounds per day which equals two tons per day, or minimally 1,000,000 pounds the equivalent of 500 tons per year. The data suggested that some water delivery people average 220 bottles per day or 8,800 pounds which equals 4.4 tons per day, or 2,200,000 pounds the equivalent of 1,100 tons per year. It was found that when the water delivery person lifts 1,000,000 pounds of items close to the body then the spine sees force that is half the weight, or 500,000 pounds of force; when 45° away from the body, the spine sees forces two times the weight, or 2,000,000 pounds of force; and when 90° away from the body, the spine sees forces four times the weight, or 4,000,000 pounds of force.

According to Backpack finite mathematical studies: when a regular person carries 1 pound in a backpack: with a straight spine, the spine sees 7 pounds of force; when the person leans forward 10°, the spine sees 9 pounds of force; when the person leans forward 20°, the spine sees 12 pounds of force; when the person leans forward 40°, the spine sees 15 pounds of force.

In case, when a regular person carries 5,000 pounds of weight per year in a backpack: with a straight spine, the spine sees 35,000 pounds of force; when the person leans forward 10°, the spine sees 45,000 pounds of force; when the person leans forward 20°, the spine sees 60,000 pounds of force; when the person leans forward 40°, the spine sees 75,000 pounds of force.

In case, when a regular person carries 18,000 pounds of weight per year in a backpack: with a straight spine, the spine sees 126,000 pounds of force; when the person leans forward 10°, the spine sees 162,000 pounds of force; when the person leans forward 20°, the spine sees 216,000 pounds of force; when the person leans forward 40°, the spine sees 270,000 pounds of force.

When a student carries one book in a backpack: with a straight spine, the spine sees 7 books of force; when the person leans forward 10°, the spine sees 9 books of force; when the person leans forward 20°, the spine sees 12 books of force; when the person leans forward 40°, the spine sees 15 books of force.

In case, when a person carries 100 pounds in a backpack: with a straight spine, the spine sees 700 pounds of force; when the person leans forward 10°, the spine sees 850 pounds of force; when the person leans forward 20°, the spine sees 1200 pounds of force; when the person leans forward 40°, the spine sees 1500 pounds of force.

When a soldier carries 100 pounds in a backpack: with a straight spine, the spine sees 700 pounds of force; when the soldier leans forward 10°, the spine sees 850 pounds of force; when the soldier leans forward 20°, the spine sees 1200 pounds of force; when the person leans forward 40°, the spine sees 1500 pounds of force.

When a person carries 1,000,000 pounds of weight per year in a backpack: with a straight spine, the spine sees 7,000,000 pounds of force, per year; when the person leans forward 10°, the spine sees 8,500,000 pounds of force, per year; when the person leans forward 20°, the spine sees 12,000,000 pounds of force, per year; when the person leans forward 40°, the spine sees 15,000,000 pounds of force per year.

In the study was also determined the belly fat forces on the spine. It was found that in the U.S., more than two-thirds of adults (220 million-plus) are overweight or obese, and childhood obesity affects 13.7 million children. As of 2016, 1.9 billion adults were overweight or obese globally. It is known that obesity, or the fat content of the belly, is associated with inflammation, diabetes, hypertension, heart conditions, metabolic syndrome, and backpain. Adipose tissue is linked to an increased risk and aggressiveness of cancer. In the study, it was sought to assess the forces that belly fat exerts on the spine with an increase in waist circumference. Using data from the Dallas Heart Study, Grundy et al. calculated belly fat mass according to waist circumference by ethnicity and sex. Using a finite element analysis, our study specifically placed the abdominal fat masses into position in the abdomen. Then, we calculated the lever arm forces seen by the spine.

In the study, it was found that in women, the average magnitude of forces generated by abdominal fat to the lumbar spine ranged between 5 to 170 pounds of force in our measurements. The average woman with a: 25 inches waist circumference exerts 5 pounds of force to the spine; 30 inches waist circumference exerts 22 pounds of force to the spine; 35 inches waist circumference exerts 41 pounds of force to the spine; 40 inches waist circumference exerts 62 pounds of force to the spine; 45 inches waist circumference exerts 77 pounds of force to the spine; 50 inches waist circumference exerts 95 pounds of force to the spine; 55 inches waist circumference exerts 114 pounds of force to the spine; 60 inches waist circumference exerts 132 pounds of force to the spine; 65 inches waist circumference exerts 150 pounds of force to the spine; and 70 inches waist circumference exerts 170 pounds of force to the spine. Also, it was found that black women had significantly greater belly fat forces than White ($P<0.004$) and Hispanic women ($P<0.02$), while there was no significant difference between White and Hispanic women ($P<0.9$).

In the same study, it was found that in men, the average magnitude of forces generated by abdominal fat to the lumbar spine ranged between 5 to 120 pounds of force in our measurements. The average man with a: 25 inches waist circumference exerts 3 pounds of force to the spine; 30 inches waist circumference exerts 12 pounds of force to the spine; 35 inches waist circumference exerts 25 pounds of force to the spine; 40 inches waist circumference exerts 39 pounds of force to the spine; 45 inches waist circumference exerts 51 pounds of force to the spine; 50 inches waist circumference exerts 65 pounds of force to the spine; 55 inches waist circumference exerts 79 pounds of force to the spine; 60 inches waist circumference exerts 93 pounds of force to the spine; 65 inches waist circumference exerts 107 pounds of force to the spine; 70 inches waist circumference exerts 120 pounds of force to the spine. Also, it was found that the Black men had significantly greater belly fat forces than White ($P<0.009$) and Hispanic men ($P<0.007$), while there was no significant difference between White and Hispanic men ($P<0.17$).

Women have complained about the pain caused by big breasts since the dawn of humanity. Large breasts have been associated with physical complaints of back pain and neck pain, yet many people question the truthfulness of women suffering with this kind of discomfort. The magnitude of the forces generated by the breast to the thoracic spine ranged between 9 pounds of force for underwire size 30 to 110 pounds of force for underwire size 60, in the erect neutral spine position. Underwire sizes: 30 inches=US 32A, 30B, 32C exerts 9 pounds of force to the spine; 32 inches=US 34A, 32B, 30C, 28D exerts 11 pounds of force to the spine; 34 inches=US 36A, 34B, 32C, 30D, 28E exerts 15 pounds of force to the spine; 36 inches=US 38A, 36B, 34C, 32D, 30E, 28F exerts 18 pounds of force to the spine; 38 inches=US 40A, 38B, 36C, 34D, 32E, 30F, 28G exerts 23 pounds of force to the spine; 40 inches=US 42A, 40B, 38C, 36D, 34E, 32F, 30G, 28H exerts 28 pounds of force to the spine; 42 inches=US 44A, 42B, 40C, 38D, 36E, 34F, 32G, 30H, 28I exerts 32 pounds of force to the spine; 44 inches=US 44B, 42C, 40D, 38E, 36F, 34G, 32H, 30I, 28J exerts 38 pounds of force to the spine; 46 inches=US 44C, 42D, 40E, 38F, 36G, 34H, 32I, 30J, 28K exerts 43 pounds of force to the spine; 48 inches=US 44D, 42E, 40F, 38G, 36H, 34I, 32J, 30K, 28L exerts 53 pounds of force to the spine; 50 inches=US 44E, 42F, 40G, 38H, 36I, 34J, 32K, 30L, 28M exerts 59 pounds of force to the spine; 52 inches=US 44F, 42G, 40H, 38I, 36J, 34K, 32L, 30M, 28N exerts 70 pounds of force to the spine; 54 inches=US 44G, 42H, 40I, 38J, 36K, 34L, 32M, 30N, 28O exerts 77 pounds of force to the spine; 56 inches=US 44H, 42I, 40J, 38K, 36L, 34M, 32N, 30O, 28P exerts 87 pounds of force to the spine; 58 inches=US 44I, 42J, 40K, 38L, 36M, 34N, 32O, 30O, 30P exerts 102 pounds of force to the spine; and 60 inches=US 44J, 42K, 40L, 38M, 36N, 34O, 32P exerts 110 pounds of force to the spine. When the person tilts over 20°, then the forces are multiplied 1.4×.

SUMMARY OF THE INVENTION

The following presents a simplified summary of one or more embodiments of the present invention in order to provide a basic understanding of our invention. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a novel dynamic, anatomic, postural, and conforming spine force modulating assembly that overcomes the drawbacks with conventional orthopedic back supports.

Another object of the present invention is that the spine force modulating assembly is stiff enough to support the spine and to distribute the load from the spine and onto the spine force modulating assembly.

Another object of the present invention is to define that the spine force modulating assembly is flexible enough not to prevent the movement of the person, nor to immobilize the spine.

Another object of the present invention is to define that the assembly can provide for correcting the posture in the chest and the abdomen and therefore take advantage of all the spine force reduction capabilities.

Another object of the present invention is to define that the spine force modulating assembly is comfortable and easy to attach.

Another object of the present invention is to define that the spine force modulating assembly is light in weight and durable.

In one aspect, disclosed is a novel dynamic, postural, anatomic, and conforming spine force modulating assembly and a method for supporting a human spine. The spine force modulating assembly comprising a frame of a length proportional to a distance between a third thoracic spine bone and a first sacral spine bone of a spine of a wearer of the spine force modulating assembly, wherein the frame is of a "S" shape and configured to support a spine portion between the third thoracic spine bone and the first sacral spine bone. The frame has an upper end and a lower end, wherein the spine force modulating assembly further comprises a pair of shoulder straps extending from near the upper end of the frame and a pair of waist straps extending from near the lower end of the frame. The frame is made from carbon fibers. The carbon fibers are oriented at about 45 degrees from a longitudinal axis.

These and other objects and advantages of the embodiments herein and the summary will become readily apparent from the following detailed descriptions taken in conjunction with the accompanying drawings.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
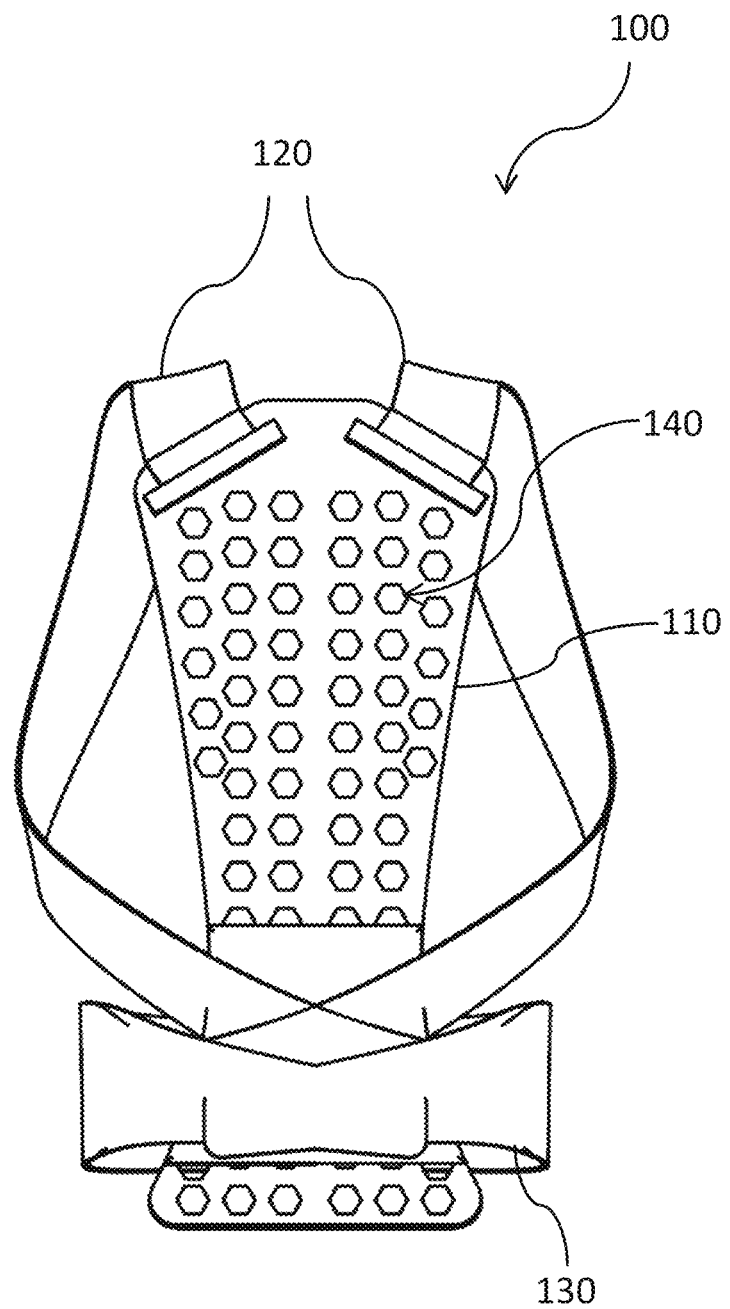
FIG. 1 is a front view of the spine force modulating assembly, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a novel, dynamic, postural, anatomic, and conforming spine force modulating assembly that can be ergonomically harnessed to the body in such a fashion as to diminish the forces seen by the cervical, thoracic, lumbar, and sacral spines of people during their activities. The disclosed spine force modulating assembly can diminish the forces on spine seen in day-to-day conditions of postural loading. The disclosed spine force modulating assembly can help people who lift loads in day-to-day life diminish spine forces seen by the spine and therefore to prevent or treat back pain. Backpack wearers, especially children and the military can use the disclosed spine force modulating assembly for preventing backs pains and balancing the forces on spine due to movement of the body or lifting of weights. The disclosed spine force modulating assembly can assist people with spinal bone loss conditions such as osteoporosis or other conditions when there is weakening of the bone.

The disclosed spine force modulating assembly can embrace and absorb the unhealthy spinal forces observed in large abdomens as in obesity; deformities such as excessive thoracic kyphosis called hunch back, excessive lumbar lordosis called sway back, lack of lumbar lordosis called flat back, scoliosis, bone weakening conditions such as osteopenia and osteoporosis, degenerative disc disease, spondylolysis and spondylolisthesis, and spinal stenosis.

In one aspect, the disclosed spine force modulating assembly can improve the alignment of the person by enhancing the person's posture: standing erect (X-plane correction), standing taller (Y-plane correction), and opening the chest, embracing proper thoracic kyphosis, proper lumbar lordosis, tightening waist circumference and pelvic tilting (Z-plane corrections). The disclosed assembly can support the spine and distribute or balance the forces exerted on to the spine. The disclosed assembly can increase the efficiency of the load carrying capability of the body while diminishing the stresses seen by the spine. The disclosed assembly allows freedom of range-of-motion of the neck to augment better posture, improve efficiency and to fight the stiffness of aging seen in the shoulder and scapulae. The disclosed assembly allows freedom of range-of-motion of the pelvis to augment better posture, improve efficiency and to fight the stiffness of aging seen in the pelvis, the hips, and the knee joints.

Figure 2:
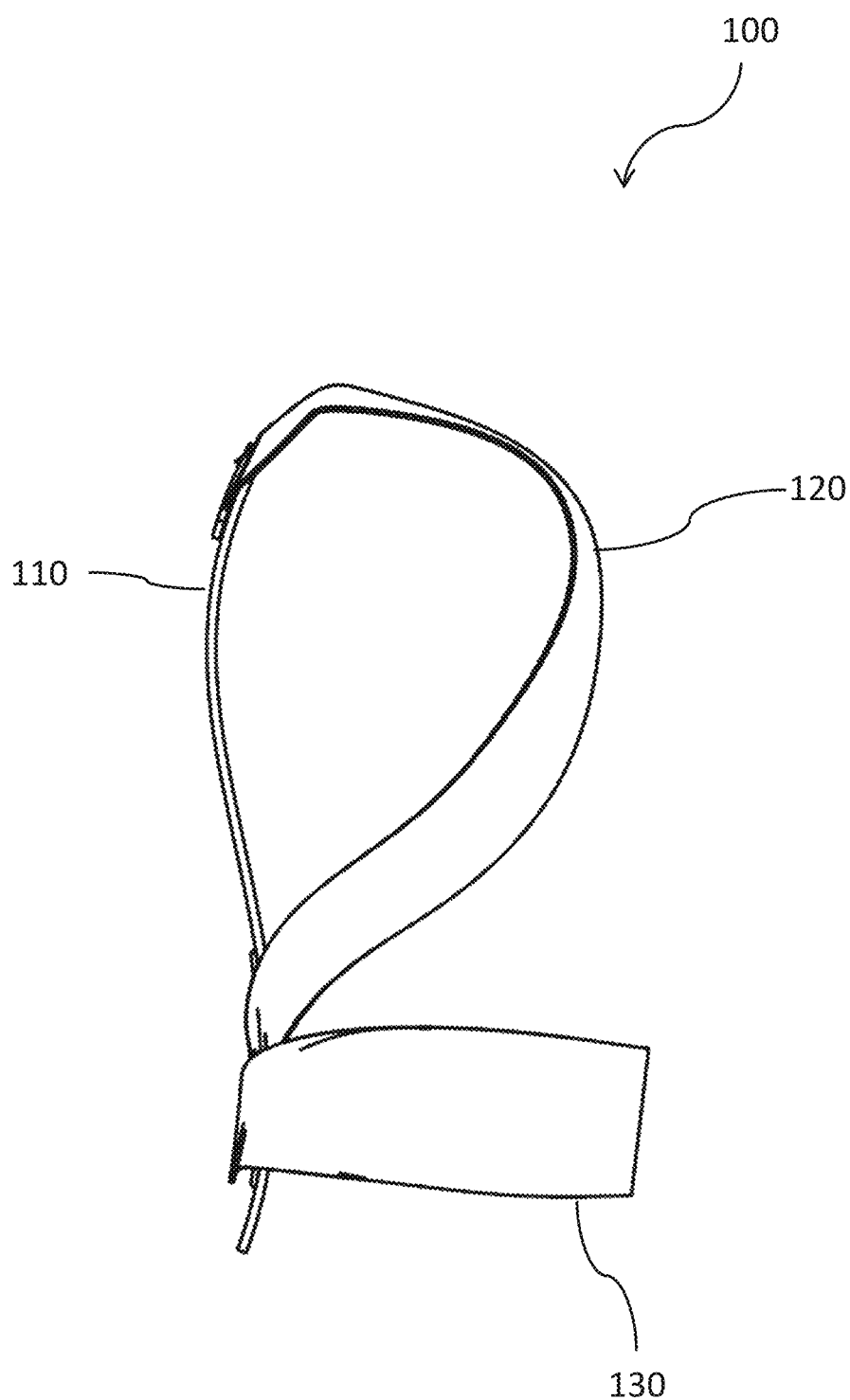
FIG. 2 is a side view of the spine force modulating assembly, according to an exemplary embodiment of the present invention.
Figure 3:
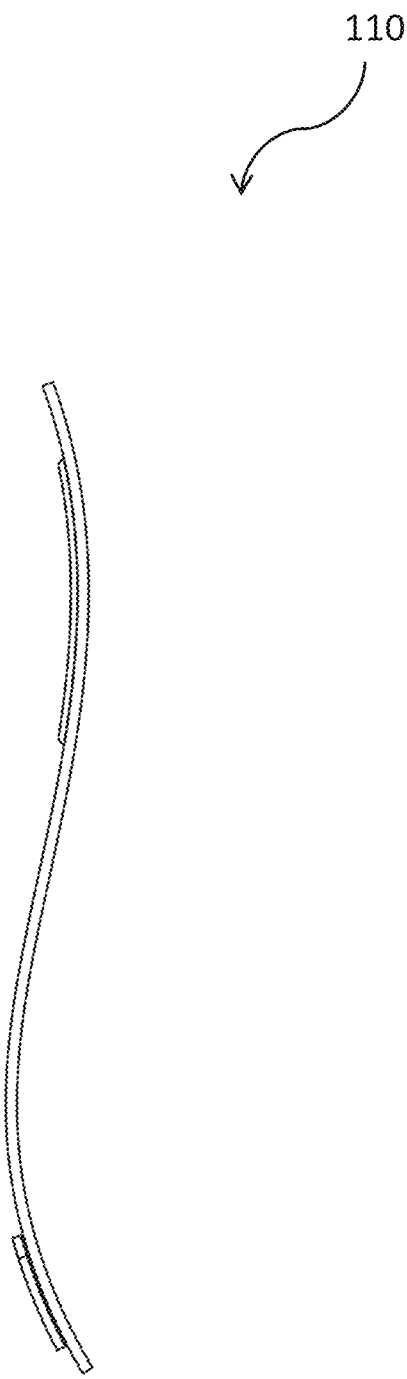
FIG. 3 is a side view of a frame of the spine force modulating assembly, according to an exemplary embodiment of the present invention.
Figure 4:
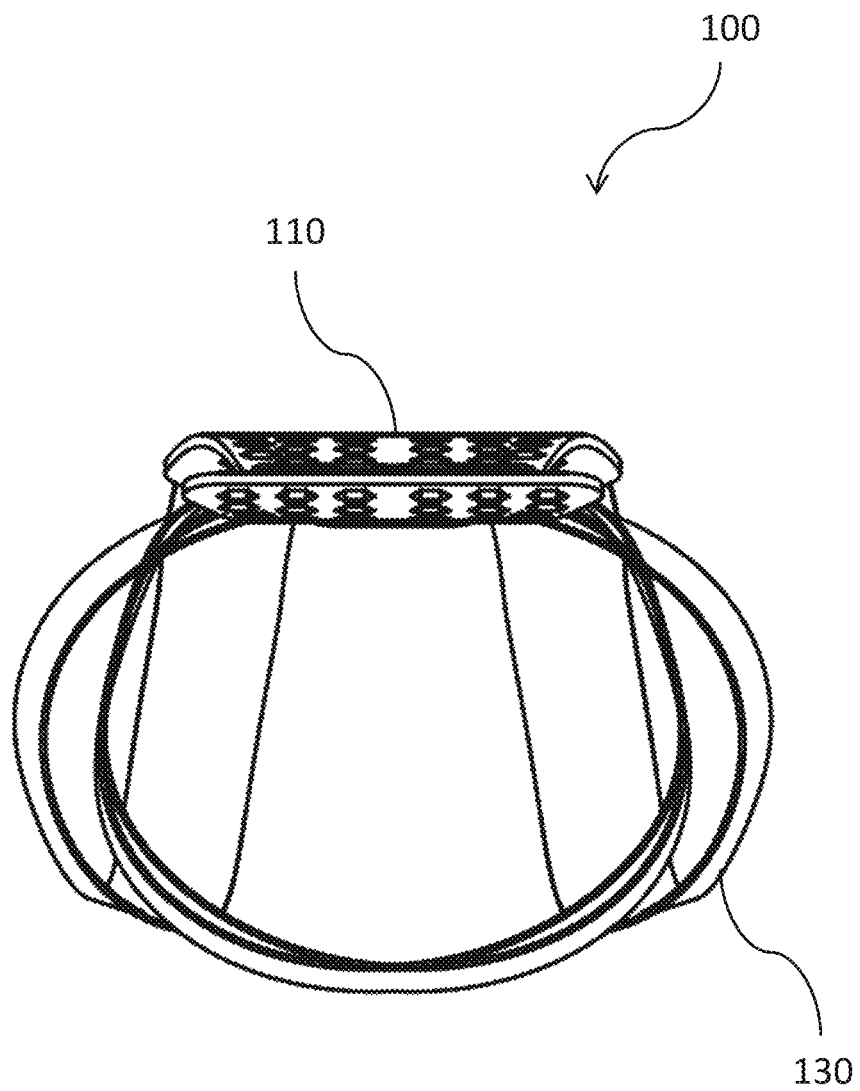
FIG. 4 is a top view of the spine force modulating assembly, according to an exemplary embodiment of the present invention.

Referring to FIG. 1 which shows an exemplary embodiment of the spine force modulating assembly 100. The spine force modulating assembly 100 includes a frame 110, the frame has an upper end and a lower end. A pair of shoulder straps 120 extends from near the upper end of the frame. A pair of waist straps 130 extends from near the lower end of the frame. The pair of waist straps can go around the waist of wearer of the disclosed assembly and the pair of shoulder straps can go around the shoulders of the wearer for securing the disclosed assembly, wherein the frame is positioned over the spine. The pair of shoulder straps and the pair of waist straps can have fasteners (not shown) for tightening and interlocking the respective straps. For example, hook and loop, or Velcro™ fasteners can be provided on ends of the pair of shoulder straps and the pair of waist straps that allows adjusting an effective length of the respective straps and securing the straps. FIG. 2 shows a side view and FIG. 4 shows the top view of the disclosed spine force modulating assembly 100.

Also shown in the drawings are the shaped holes 140 in the frame 110. The frame can have hexagonal shaped holes made throughout an area of the frame in a predefined pattern. The hexagonal shape holes in the predefined pattern may ensures strength, flexibility, and lightness in weight while being able to transmute the loads originally intended for the cervical, thoracic, lumbar, and sacral spines to the disclosed assembly. Although circular shape holes are preferred, holes of any other shape are within the scope of the present invention. For example, the holes can be hexagonal, square, round, polygonal, elliptical, triangular, and the like shapes. Also, the frame without the holes is also within the scope of the present invention, whereby the thickness of the frame 110 may be varied, along with fiber orientation in the frame of 110.

The frame 110 can have a "S" shape and designed to support predefined areas of the spine when positioned over the spine and the straps secured to the torso of the wearer. The specific shape and design of the frame allows effective balance and distribution of the forces acting on the spine, thus preventing undesired pressure on the backbone. This in turn prevents any injury to the backbone upon making a sudden body movement or lifting a weight. Moreover, the frame keeps the body aligned in proper posture and thus the backbone in healthy shape, further reducing undesired forces on the spine.

The frame can be made from various materials, such as carbon fibers, glass fibers, and Kevlar fibers. Preferably, regarding the flow and fiber arrangement: in one iteration, the carbon fiber can be organized into 45 degrees upwards placement to provide longitudinal strength in flexion and extension and to provide rotational shear resistance. Fiber orientation can vary by design when answering the need to block specific forces. The use of carbon fiber in the frame may ensure that the disclosed assembly has sufficient stiffness, and it is not heavy to wear.

The frame 110, can be of a plate profile resulting in a large moment of inertia in vertical and lateral direction. This supports the spine while bending and during torsion. When the disclosed assembly is worn, an extensive amount of load is transmitted to the disclosed assembly. The frame being made from carbon fiber is very strong and stiff. The frame can be designed to be stiff enough to support the spine and has the capability to transmit the load from the spine. This means that the frame can support the spine and can subsume or take substantial amount of load from the spine as seen in the lessening of stresses.

In one implementation, the geometry of the frame and the attachment points on the frame were designed using multiple iterations of finite elemental analysis. The finite model was developed as described below.

3D Model Development: The model used for the finite elemental analysis (FEA) simulation was based on 'BodyParts3D/Anatomography' data (Database Center for Life Science, University of Tokyo, Tokyo, Japan). The model was imported into the FEA software (described below). The model was evaluated by scanning real spine parts and then collecting the data together into one 3D model. The finite element needs a perfect fit of surfaces, and all the measurements were made to fit the contact surfaces with a range of accuracy within 0.1 mm. The spine model was physiologically accurate in accordance with the standards of the industry.

Physics setup: Altair Optistruct™ (Troy, Michigan) was used for the FEA analysis. It accounts for the deformations, stresses and reaction forces at the boundary or volume level, according to the input conditions. A nonlinear structural scheme was used. This is important since the material and geometric nonlinearities play an important role in this analysis. Several boundary conditions were applied to the initial requirements: Fixed constraint, for the bottom part of the spine (the coccyx region); body load, on the areas where the forces are exerted; contact for the areas where the vertebrae come in contact; while the solver was a stationary type to account for the required forces and stresses.

Mesh: Adequate meshing of all vital components of the spine is the key to obtaining the realistic representation of the biomechanical conditions. Because of the complexity of the shapes used in the model tetrahedral mesh with proximity refinement and aspect ratio control was used. Spinal bones and ligaments were meshed with very dense finite elements.

For obtaining the realistic stresses and strains in the disc, this area was modeled with hexahedral FEA. This means that less elements were used, and the stress and strain resolution and convergence was a lot better in these parts. The entire model contained 13M elements.

The abdominal muscles consisting of the transversus, external oblique, internal oblique, and the rectus abdominis were modeled. The paravertebral muscles were also modeled, along with the chest and shoulder muscles.

Using the above finite elemental analyses model, the frame of the disclosed spine force modulating structure was designed. The frame was made using carbon fiber. The length of the frame can be such that to support the spine portion between T3 to S1 bones i.e., from third thoracic spine (T3) encompassing lumbar spine, and up to first sacral spine bone (S1). The numbering is from top to bottom of the spine i.e., from first cervical bone (C1) and down to coccygeal. The disclosed frame can encompass the T3-T12 thoracic bones, L1-L5 lumbar bones, and the first sacral bone of the S1-S5 sacral bones. Using multiple iterations of finite elemental analyses, we designed the main support structure of a novel dynamic, postural, anatomic, conforming spine force modulating assembly for the back with carbon fiber.

To define the necessity for spine force coverage by length, we referenced the following studies and data points: NECK FORCES STUDY: According to data from Hansraj K K: *Assessment of Stresses in the Cervical Spine Caused by Posture and Position of the Head. Surgical Technology Int.* 2014 November; 25:277-9, spinal forces predominate the T3 to T7, L1 and L4 and L5 locations of the spine. BACKPACK FORCES STUDY: According to data from Hansraj K K; Hansraj J. A.; Griffin-Hansraj, M. D.; Kiernan, J.; Subesan, N., Firtat, B.; Elsisi, A.: *Backpack Forces on the Spine. Surgical Technology Int.* 2018 November; 33: 361-365, spinal forces predominate the T2 to T3, T9-T12, and L1 locations of the spine. BREAST FORCES STUDY: According to data from Hansraj K K. Breast Forces on the Spine. Surg Technol Int. 2016 April; 28:311-5, spinal forces are predominantly located at C2-T10 and T12-11 locations of the spine. BELLY FAT FORCES STUDY: According to data from Hansraj K K; Hansraj J. A.; Griffin-Hansraj, M. D.; Rozic, U.: Belly Fat Forces on the Spine: Finite Element Analyses of Belly Fat Forces by Waist Circumference Surgical Technology Int. 2022 March; 40:1-6 spinal forces are predominantly located T12-11 locations of the spine. LIFTING FORCES STUDY: According to data from Hansraj K K: Lifting Forces on the Spine. In Press, spinal forces are predominantly located T4-17, L1 and L4-L5 locations of the spine. OSTEOPOROSIS DATA: According to data from Matzkin E G, DeMaio M, Charles J F, Franklin C C, *Diagnosis and Treatment of Osteoporosis*: What Orthopaedic Surgeons Need to Know. J Am Acad Orthop Surg, 2019 Oct. 15; 27(20): e902-e912, and clinical experience in a spinal surgery practice, osteoporotic compression fractures are primarily located at T7 trough L3 while T12 and L1 are the most commonly involved levels, Few fractures occur at the upper thoracic spine T4, T5 and T6. Few fractures occur at L4 and L5. Sacral fractures are extremely rare.

DEGENERATIVE DISC DISEASE: structural failures associated with intervertebral discs are annulus tears, disc prolapse, endplate damage, disc narrowing, radial bulging, and subsequent osteophyte formation in the vertebrae. Mechanically, intervertebral discs are found to be vulnerable to compression, flexion, axial rotation, and complex loading mechanisms through single impact, cyclical, and continuous loading. The L4-L5 level has the highest probability of being involved, followed by multiple discs involvement of the lumbar spine. Thoracic disc involvement is clinically noted in the mid thoracic spine most commonly based upon clinical experience.

HERNIATION OF AN INTERVERTEBRAL DISC: The L4-L5 level has the highest probability of being involved, followed by the L5-S1 and L3-L4 involvement of the lumbar spine. Thoracic disc herniation involvement is clinically noted in the lower thoracic spine mostly based upon clinical experience.

SPINAL STENOSIS: In the cervical spine, the bottom two levels C5-6 and C6-7 are most involved. While spinal stenosis may occur throughout the spine, it is most noted in the lumbar spine at the L3-4, L4-5.

SPONDYLOLISTHESIS: In the cervical spine the bottom C4-05 is most commonly involved. While spinal stenosis may occur throughout the spine, it is most noted in the lumbar spine at the L4-5, L5-S1 and L3-L4.

SCOLIOSIS: A very common curve called the right thoracic curve may have an apex at T7 or T8 and a compensatory lumbar curve with an apex at L2 or L3.

AGING AND THE SPINE: With aging anterior tilting of the head and plumbline of the body moves the body anterior to the femoral head further unbalancing the spine leading to the generation of unbalanced thoracic and lumbar spine forces. The thoracic kyphosis is increased yielding a larger curve. The lumbar lordosis is increased leading to a larger curve. The body compensates by flexing the hip joints leading to a shorter person and hip stiffness. The knee joints similarly flex, leading to a shorter person and knee stiffness. Major shifting occurs in thoracic kyphosis and lumbar lordosis over time.

The disclosed frame does not support the cervical bones in order to allow freedom of range-of-motion of the neck to allow for flexibility of the spine and to take advantage of the efficiencies noted in the cervical spine study. Freedom of range-of-motion augments better posture and helps to fight the stiffness of aging seen in the shoulder and scapulae. Similarly, the frame does not support the most of sacral bones and the pelvis to allow freedom of range-of motion of the pelvis (Z or depth motion). This freedom enhances posterior pelvic tilting which is more efficient in lifting objects. Anterior and posterior pelvic tilting enhances walking further in conditions such as lumbar spinal stenosis. Pelvic freedom range-of-motion augments better posture and helps to fight the stiffness of aging seen in the pelvis, the hips, and the knee joints.

Besides the length of the frame, the width of the frame was also optimized. The frame can cover the width of the vertebral body and extend laterally to cover the width of the vertebral body and the erector spinae muscles—the iliocostalis, the longissimus, the spinalis, rhomboid major and minor. These paravertebral muscles are subsequently covered by the superficial muscles called the trapezius and latissimus dorsi muscles.

In the experiments, an Assessment of Young's Modulus in the setup of the experiment was made. The disclosed assembly provided material strength:12,000 MPa: elastic modulus of cortical vertebral bone; 200 MPa: elastic modulus of cancellous vertebral bone; 3500 MPa: elastic modulus of posterior cortical vertebral bone; 8 MPa: elastic modulus of annulus fibrosus of the intervertebral disc; 8 MPa: elastic modulus of annulus matrix of the intervertebral disc; 4 MPa: elastic modulus of nucleus pulposus of intervertebral disc; 450 MPa: elastic modulus of collagen matrix of intervertebral disc; 7.8 MPa: elastic modulus of anterior longitudinal ligament; 10 MPa: elastic modulus of posterior longitudinal ligament; 17 MPa: elastic modulus of lateral facet ligament; 10 MPa: elastic modulus of inter-spinous ligament; 8 MPa: elastic modulus of supra-spinous ligament; 10 MPa: elastic modulus of inter-transverse ligament; 105,000 MPa: elastic modulus of carbon fiber; 36,000 MPA: elastic modulus of glass fiber; 28,000 MPA: elastic modulus of kevlar; 10,000 MPA: elastic modulus of nylon.

After several iterations in the experiment, the height, width, thickness, and anatomical shape of the frame was designed. The frame was designed with use of state-of-the-art numerical analysis using finite element method, which was enhanced with a topology optimization subroutine.

The frame was designed by use of topology optimization for balancing the stiffness, flexibility, and strength. The length of the frame was designed using finite element studies to determine where the forces were. The width of the frame was designed by matching the vertebral body and corresponding paravertebral muscles. The shape of the frame was designed by matching the thoracic curvature and lumbar curvature in various age groups and spinal conditions. Topographic analyses yielded various renderings for variability of the flexibility of the frame. Topographical optimizations were utilized to create a surface that interfaces with the thoracic and lumbar spines. This is to say that the surface forces were dispersed equally across the assembly.

Topology Optimization:

The stiffness and strength provided by the carbon fiber material will be explained in the next section. The hexagonal shapes in this iteration are there to provide sufficient flexibility and spine force modulating, hence decreasing the stresses in the spine upon loading. The mathematical and numerical background of the topology optimization is described below.

Topology Optimization Theory:

The general mathematical concepts used to formulate the structural topology and shape optimization problems during this work is explained here. A brief introduction to structural optimization is first presented which is followed by an explanation of topology optimization. To formulate the structural optimization problem, an objective function, design variables and state variables needs to be introduced. The objective function (f) represents an objective that could either be minimized or maximized. A typical objective could be the stiffness or volume of a structure. Furthermore, some structural design domains and state variables associated to the objective function needs to be defined. The design variables (x) describe the design of the structure, it may represent the geometry. The state variables (y) represent the structural response which can for example be recognized as stress, strain or displacement. Furthermore, the state variables depend on the design variables y(x). The objective function is subjected to design and state variable constraints to steer the optimization to a sought solution.

$$\begin{cases} \min_x & f(x, y(x)) \\ \text{subject to} & \begin{cases} \text{design constraint on } x \\ \text{state constraint on } y(x) \\ \text{equilibrium constraint} \end{cases} \end{cases}$$

A state function g(y) that represents the state variables can be introduced, for example a displacement in a certain direction. This state function can be incorporated as a constraint to the optimization task, where it is usually formulated such that $g(y) \leq 0$. Consider the case where g(y) is represented by a displacement vector g(u(x)) in a discrete finite element problem. To establish the state function, this requires that nodal displacement is solved for:

$$u(x) = K(x)^{-1} f(x)$$

where K is the global stiffness matrix and f is the global load vector. This means that the optimization task can be expressed in a so-called nested formulation where the equilibrium constraint is taken care of by the state function formulation:

$$\begin{cases} \min_x & f(x) \\ \text{subject to} & g(u(x)) \leq 0 \end{cases}$$

The optimization task presented in equation is called simultaneous formulation in comparison. This equation is usually solved by evaluating derivatives of f and g with respect to x. In this context, x will represent a geometrical feature. Based on what geometrical feature that is parametrized, the structural optimization problem can be classified into:

Size optimization: the design variable x, represents a structural thickness such as a distributed thickness or a cross-sectional area of a truss model that can be varied. The optimal thickness typically minimizes some physical quantity such as the strain energy(compliance) or the deflection, while the equilibrium constraint has to be fulfilled. The state function may then have a relative volume.

Shape optimization: the design variable x, represents the boundary of the state equation. In this case, the boundary of the considered domain x could vary such that some physical quantity is minimized.

Topology optimization: the design variable x, represents the connectivity of the domain. It involves features such as number and sizes of holes in the design domain. The objective function can also be formulated using several objectives, it is then often called a multi-objective or a vector optimization problem:

$$\min_x f(f_1(x, y), f_2(x, y), \ldots, f_n(x, y))$$

where n is the number of objective functions. Since all objectives are minimized with respect to x and y, a global optimum is not distinct. The objectives can be formulated as a scalar formulation of the objective functions using weights.

$$f = \sum_i f_i w_i$$

Where "i" is the single objective function index and the total sum of the set of weights are:

$$\sum_i w_i = 1$$

By varying the set of weights, different so-called Pareto optimal points can be found where these solutions are unique with respect to the associated weight set. The set of different Pareto optimal points gives a Pareto set, where no objective can be improved without worsening another. We seek an optimal placement of material points where the reference domain is partitioned into void and solid elements by a finite element discretization.

In mathematical terms we seek an optimal subset $\Omega$ mat $\subset \Omega$. Where $\Omega$ is an available design domain. The design variable x is now represented by the density vector $\rho$ containing elemental densities $\rho e$. The local stiffness tensor E can be formulated by incorporating $\rho$ as an integer formulation.

$$E(\rho) = \rho E^0$$

$$\rho_e = \begin{cases} 1 & \text{if } e \in \Omega_{mat} \\ 0 & \text{if } e \in \Omega \backslash \Omega_{mat} \end{cases}$$

and a volume constraint $$\int_\Omega \rho d\Omega = \text{Vol}(\Omega_{mat}) \leq V$$

V is the volume of the initial design domain. When $\rho e=1$, we consider an element to be filled whereas an element with $\rho e=0$ is considered to be a void element. To use a gradient based solution strategy for the optimization problem, the integer problem described needs to be formulated as a continuous function so that the density function can take values between 0 and 1. The most common method to relax the integer problem is the SIMP (Solid Isotropic Material with Penalization) method. The density function is then written as:

$$E = \rho^p E^0, \rho \in [\rho_{min}, 1], p > 1$$

where p is the penalizing factor that penalizes elements with intermediate densities to approach 0 or 1, $\rho_{min}$ is the lower density value limit to avoid singularities. Thus, the penalization is achieved without introducing any explicit penalization scheme. For materials with Poisson ratio v=0.3, it is recommended to use p≥3. In our case, we employed design with the use of the advanced topology algorithm to come up with the shape of our structure.

With regard to age differences and the anatomic matching of the thoracic curvature and lumbar curvature of the spine, the main frame was designed with optimized matching of the thoracic and lumbar curves. These curvatures vary with age as noted in our aging of the spine modelling. While the original design modulates 30 degrees of thoracic kyphosis, and 30 degrees of lumbar lordosis as a model for younger spines, older spines are modelled according to our modelling of the aging spine presented before which can be 40 degrees of thoracic kyphosis and 40 degrees of lumbar lordosis, or 45 degrees of thoracic kyphosis and 45 degrees of lumbar lordosis, or 50 degrees of thoracic kyphosis and 50 degrees of lumbar lordosis as examples. The assembly can be made for custom sizes.

The straps help to position the frame, secure the assembly to the back, and also help in the weight distribution. The shoulder straps connect the frame to the upper torso. Once secured, the frame can be retained by friction and the normal force between the frame, the straps, and the body. The upper shoulder straps serve to bring the shoulders back and open up the chest which improves posture. Proper posture supplies a measurable improvement in spine forces. When strapped the person's chest conforms to the thoracic curvature built into the brace. The upper straps improve the posture of the person by enhancing the person's posture standing erect (X-plane correction), standing taller (Y-plane correction) and the opening of the chest, embracing proper thoracic kyphosis, and subsequent lumbar lordosis (Z-plane corrections) which leads to scalable spine force reductions as noted in the text neck study, the backpack study, and the breast forces study. The shoulder straps are designed for strength and ability to modify posture. The areas above the shoulder are specifically designed to provide more cushion and comfort. The areas underneath the armpit are designed out of material that enhances hygiene.

As an iteration, the straps utilize hook and loop fastener for fastening. The hook and loop fastener are in contact with the straps. The hook and loop fastener are suitable for this application since it makes the attachment of the strap of the novel dynamic, anatomic, postural, conforming spine force modulating assembly user-friendly and is perfect for carrying shear loads. The straps in one iteration, are made of elastic polyproline to ensure sufficient strength and comfort, with Velcro™ as an option for tightening.

The waist straps can harness the assembly to the abdomen and lumbar spine. The goal is to diminish the abdominal circumference and diminish the belly fat forces on the spine as defined in the belly fat forces on the spine data. When strapped, the person's lower back conforms to the lumbar curvature built into the frame. The lower strap stabilizes the person to the frame allowing for improvement of the alignment of the person by enhancing the person's posture; standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the assembly.

The lower waist strap provides a wrap that tightens the belly and diminishes the waist circumference, a concept called "hug". The straps are designed to be wider to provide more surface area, more friction, diminished waist circumference and enhanced posterior pelvic tilting. When the waist circumference is diminished, further force reductions occur, as defined by the belly fat forces on the spine study. The lower portion of the waist strap when engaged allows the pelvis to be tilted towards the belly, a rotation of the pelvis called posterior pelvic tilting, and may be called a "tuck". This freedom enhances posterior pelvic tilting which is more efficient in lifting objects. Anterior and posterior pelvic tilting enhances walking further in conditions such as lumbar spinal stenosis.

The disclosed assembly is a novel dynamic, postural, anatomic, and conforming spine force modulating structure for the back. It includes features to conform to proper postures of the thoracic and lumbar spines in young and old spines and in special custom cases. Special emphasis was placed on human comfort, especially in the modes of attachment, with modifiable options. The disclosed assembly is made to be as light as possible and made from reliable, comfortable, and long-lasting materials. The disclosed assembly may allow the back to be stiff enough to support the spine, to transmute the loading from the spine and place the spine forces on to the frame. At the same time, to be flexible enough to allow the movement of the subject. The movement of the subject's spine provides inherent flexibility and human comfort. The disclosed assembly can be made from materials that are very light and very strong. It ensures that the conforming back support assembly has sufficient stiffness and is not heavy to wear.

Figure 5:
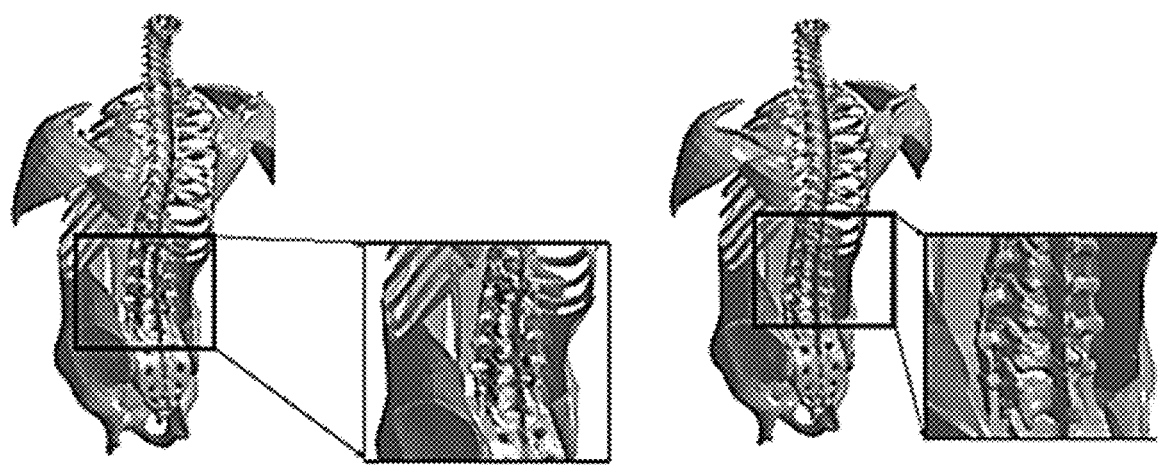
FIG. 5 shows comparison of the stresses without (left) and with (right) the disclosed assembly, according to an exemplary embodiment of the present invention.

The disclosed assembly was evaluated, and the force results are shown in FIG. 5: FIG. 5 shows the comparison of the stresses without (left) and with (right) a novel dynamic, postural, anatomic, conforming spine force modulating structure. When the spine is loaded in this instance with the disclosed assembly, the stresses in the spine are significantly lower with the assembly than without the assembly. This example is of the 50 lbf. load at the offset of 300 mm at the back. The results are shown in Table 1 below.

TABLE 1

| | Force results | | |
|---|---|---|---|
| | No assembly | With assembly | Improvement |
| Stress (MPa) | 7.2 | 0.8 | 89% |
| Displacement(mm) | 11.3 | 3.8 | 67% |

Here the values that are presented in the previous photos are mathematically compared. We assessed at the maximum stresses and maximum deformation noted in the spine with and without a novel dynamic, postural, anatomic, conforming spine force modulating structure. A novel dynamic, postural, anatomic, conforming spine force modulating structure for the back gave us the 89% decrease in peak stress in the spine and also resulted in the 67% decrease in deformation, which implies a 67% higher stiffness and support. This example is of the 50 lbf. load at the offset of 300 mm at the back.

Figure 6:
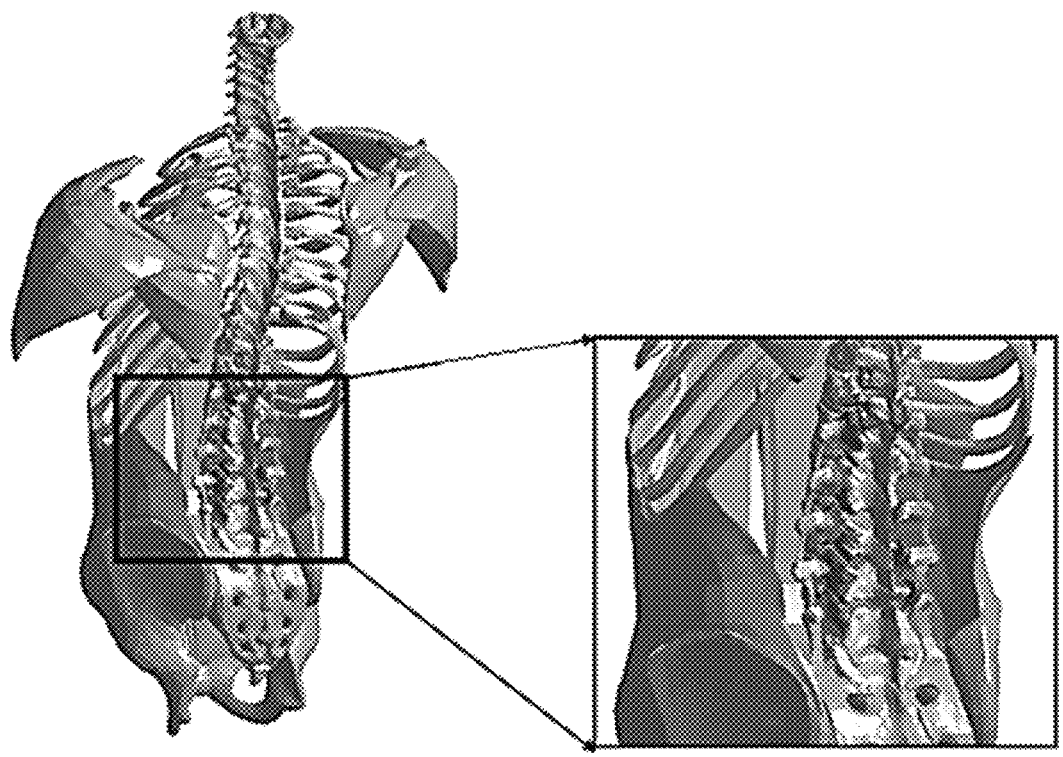
FIG. 6 shows the force results from non-use of the disclosed assembly, according to an exemplary embodiment of the present invention.

Referring to FIG. 6 which shows a model resulting from non-use of the disclosed assembly. Loading the spine without a novel dynamic, postural, anatomic, conforming spine force modulating structure—stresses are noted in the spine. The spine model was loaded, and findings were in accordance with the data from table 2. Table 2 shows the loading of the spine without the disclosed assembly. Stress is noted graphically in red and measured in MPa as noted. This example is of the 50 lbf. load at the offset of 300 mm at the back.

TABLE 2

Force results of loading of the spine without the disclosed assembly.

| Load (lb) | Load (N) | Von Mises Stress (Mpa) | Added Reaction force (lbf) | Added Reaction force (N) | Reaction moment (Nm) | Von Mises Stress (Mpa) | Added Reaction force (lbf) | Added Reaction force (N) | Reaction moment (Nm) |
|---|---|---|---|---|---|---|---|---|---|
| 1 | 4.45 | 0.107 | 7.1 | 31.6 | 0.167 | 0.118 | 8.6 | 38.1 | 0.247 |
| 5 | 22.25 | 0.535 | 35.5 | 158 | 0.835 | 0.59 | 42.8 | 190.5 | 1.235 |
| 10 | 44.5 | 1.07 | 71.0 | 316 | 1.67 | 1.18 | 85.6 | 381 | 2.47 |
| 15 | 66.75 | 1.605 | 106.5 | 474 | 2.505 | 1.77 | 128.4 | 571.5 | 3.705 |
| 20 | 89 | 2.14 | 142.0 | 632 | 3.34 | 2.36 | 171.2 | 762 | 4.94 |
| 25 | 111.25 | 2.675 | 177.5 | 790 | 4.175 | 2.95 | 214.0 | 952.5 | 6.175 |
| 50 | 222.5 | 5.35 | 355.1 | 1580 | 8.35 | 5.9 | 428.1 | 1905 | 12.35 |
| 75 | 333.75 | 8.025 | 532.6 | 2370 | 12.525 | 8.85 | 642.1 | 2857.5 | 18.525 |
| 100 | 445 | 10.7 | 710.1 | 3160 | 16.7 | 11.8 | 856.2 | 3810 | 24.7 |
| 200 | 890 | 214 | 1420.2 | 6320 | 33.4 | 23.6 | 1712.4 | 7620 | 49.4 |
| 300 | 1335 | 32.1 | 2130.3 | 9480 | 50.1 | 35.4 | 2568.5 | 11430 | 74.1 |
| 400 | 1780 | 42.8 | 2840.4 | 12640 | 66.8 | 47.2 | 3424.7 | 15240 | 98.8 |
| 500 | 2225 | 53.5 | 3550.6 | 15800 | 83.5 | 59 | 4280.9 | 19050 | 123.5 |

| Load (lb) | Load (N) | Von Mises Stress (Mpa) | Added Reaction force (lbf) | Added Reaction force (N) | Reaction moment (Nm) | Von Mises Stress (Mpa) | Added Reaction force (lbf) | Added Reaction force (N) | Reaction moment (Nm) |
|---|---|---|---|---|---|---|---|---|---|
| 1 | 4.45 | 0.293 | 10.9 | 48.7 | 0.453 | 0.609 | 14.6 | 64.8 | 1.0 |
| 5 | 22.25 | 1.465 | 54.7 | 243.5 | 2.265 | 3.045 | 72.8 | 324 | 5.1 |
| 10 | 44.5 | 2.93 | 109.4 | 487 | 4.53 | 6.09 | 145.6 | 648 | 10.2 |
| 15 | 66.75 | 4.395 | 164.2 | 730.5 | 6.795 | 9.135 | 218.4 | 972 | 15.3 |
| 20 | 89 | 5.86 | 218.9 | 974 | 9.06 | 12.18 | 291.2 | 1296 | 20.4 |
| 25 | 111.25 | 7.325 | 273.6 | 1217.5 | 11.325 | 15.225 | 364.0 | 1620 | 25.5 |
| 50 | 222.5 | 14.65 | 547.2 | 2435 | 22.65 | 30.45 | 728.1 | 3240 | 51.1 |
| 75 | 333.75 | 21.975 | 820.8 | 3652.5 | 33.975 | 45.675 | 1092.1 | 4860 | 76.6 |
| 100 | 445 | 29.3 | 1094.4 | 4870 | 45.3 | 60.9 | 1456.2 | 648 | 102.1 |
| 200 | 890 | 58.6 | 2188.8 | 9740 | 90.6 | 121.8 | 2912.4 | 12960 | 204.2 |
| 300 | 1335 | 87.9 | 3283.1 | 14610 | 135.9 | 182.7 | 4368.5 | 19440 | 306.3 |
| 400 | 1780 | 117.2 | 4377.5 | 19480 | 181.2 | 243.6 | 5824.7 | 25920 | 408.4 |
| 500 | 2225 | 146.5 | 5471.9 | 24350 | 226.5 | 304.5 | 7280.9 | 32400 | 510.5 |

Figure 7:
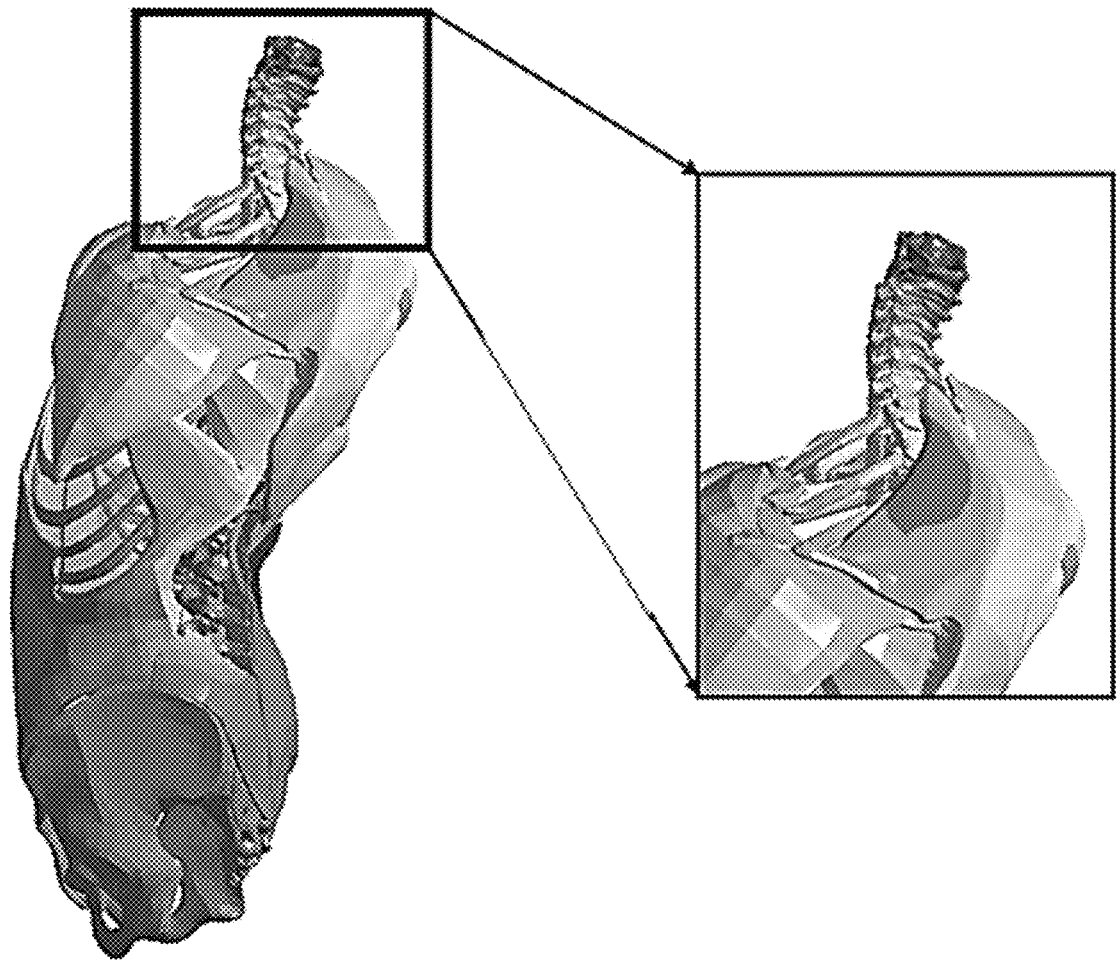
FIG. 7 shows the force results from a loaded spine without the disclosed assembly, according to an exemplary embodiment of the present invention.

Referring to FIG. 7 which shows the result of loading the spine without the disclosed assembly. As shown, displacement is noted in the spine. A simulation was performed of the deformation of the spine without the disclosed assembly. The deformation is most changed at the areas in orange. The more the spine deforms, the less stiff it is. This example is of the 50 lbf. load at the offset of 300 mm at the back.

Figure 8A:
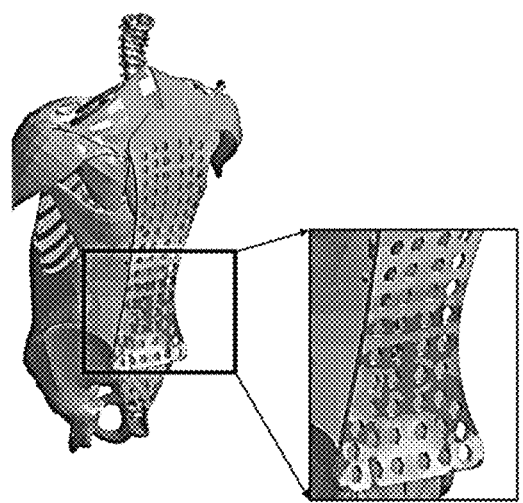
FIGS. 8A and 8B shows the force results from a loaded spine with the disclosed assembly, according to an exemplary embodiment of the present invention.
Figure 8B:
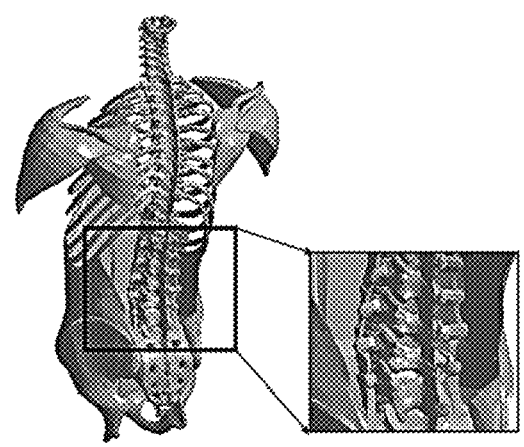

Referring to FIGS. 8A and 8B show the force results when loading the spine with the disclosed assembly—on the left the assembly transmutes most of the force from the lumbar spine, on the right a minimal stress noted in the spine. When the spine is loaded in this instance with disclosed assembly, the stresses are noted to be carried by the frame. An evaluation of the spine shows that the frame carries the accumulated stress while the stresses in the spine have decreased substantially. The spine itself now sees very little stress.

Figure 9:
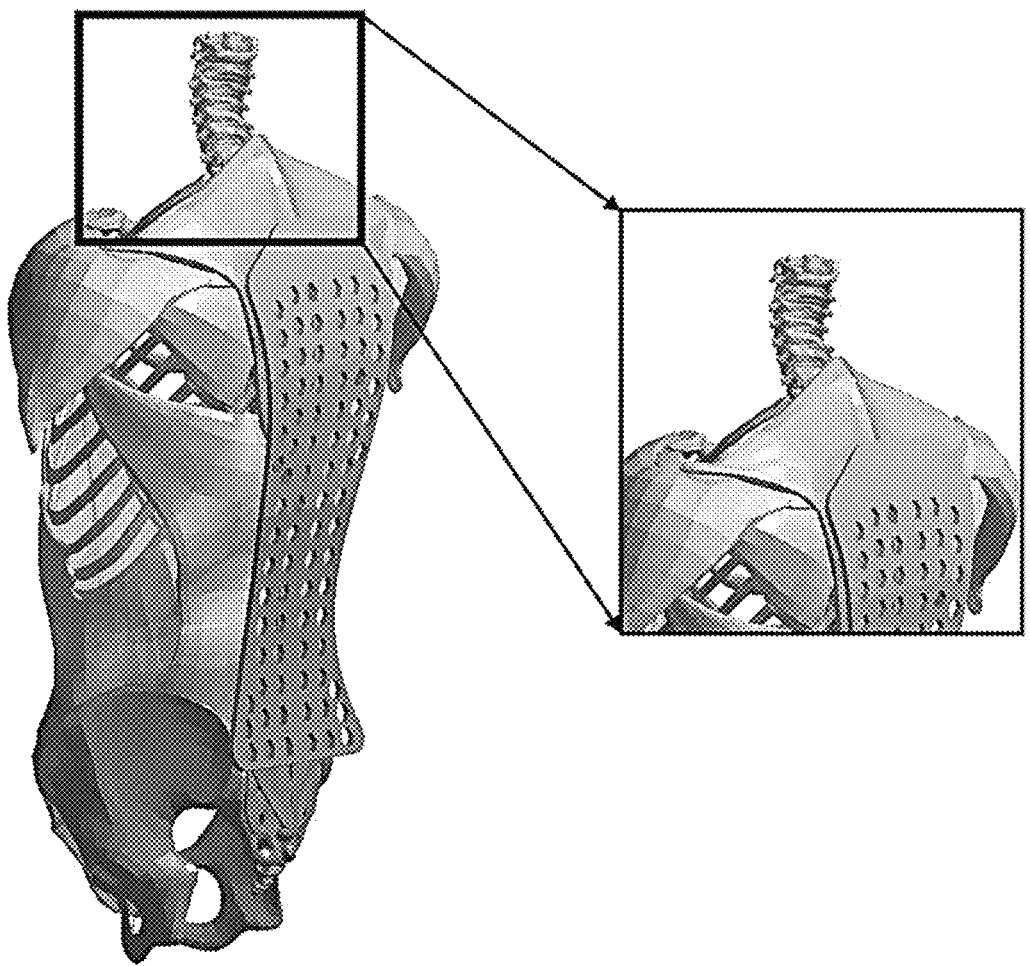
FIG. 9 shows the force results from a loaded spine with the disclosed assembly and showing the displacement in the spine, according to an exemplary embodiment of the present invention displacement noted in the spine

Referring to FIG. 9 which shows results of loading the spine with the disclosed assembly—displacement noted in the spine. When the spine is loaded in this instance with the disclosed assembly, the deformation is lower in the situation with the support structure. This speaks to the increase in stiffness provided by the spine support frame of the disclosed assembly for the back. This example is of the 50 lbf. load at the offset of 300 mm at the back.

Efficiency in Lifting Cases was also studied, and the results are discussed as follows. Using finite element assessment, a novel dynamic, postural, anatomic, conforming spine force modulating structure is shown to be 89% efficient in transmuting also known as unloading stresses to the back in this example of the 50 lbf. load at the offset of 300 mm at the back. Using the disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Assessment of delivery people who lift all day: It was found that in people who lift the weight occupationally such as a delivery person who lifts the packaging by hand, when the delivery worker lifts without the disclosed assembly: 1,000 pounds per day, this is 250,000 pounds per year; lifts 4,000 pounds per day this is 1,000,000 pounds per year; and lift 6,000 pounds per day this is 1.5 million pounds per year.

Assessment of regular people lifting 5,000 pounds per year by hand: When a regular person carries 5,000 pounds of weight per year in their hands: Unprotected, close to the body then the spine force is half the weight of the item, the force is 2,500 pounds of force to the spine. By using the disclosed assembly, the spine sees 275 lbf., and 2,225 pounds of force is transmuted. In another instance, unprotected, 45 degrees from the body then the spine force is 2× the weight, the force is 10,000 pounds of force to the spine. While using the disclosed assembly, the spine sees 1,100, and 8,900 pounds of force is transmuted. In another instance, unprotected, 90 degrees from the body then the spine force is 4× the weight of the item, the force is 20,000 pounds of force to the spine. While using the disclosed assembly, the spine sees 2,200 lbf., and 17,800 pounds of force is transmuted.

Assessing regular persons carrying 18,000 pounds per year with their hands: In this instance, unprotected, close to the body then the spine force is half the weight of the item, the force is 9,000 pounds of force to the spine. While using the disclosed assembly, the spine sees 990 lbf., and 8,010 pounds of force is transmuted. In another instance, unprotected, 45 degrees from the body then the spine force is 2× the weight, the force is 36,000 pounds of force to the spine. While using the disclosed assembly, the spine sees 3,960 lbf., and 32,040 pounds of force is transmuted. In another instance, unprotected, 90 degrees from the body then the spine force is 4× the weight of the item, the force is 72,000 pounds of force to the spine. While using the disclosed assembly, the spine sees 7,920 lbf., and 64,080 pounds of force is transmuted.

When a person carries 1,000,000 pounds of weight per year in their hands: Unprotected, close to the body then the spine force is ½ the weight of the item, the force is 500,000 pounds of force to the spine. While using the disclosed assembly, the actual force seen by the spine is 55,000 lbf. and the disclosed assembly transmuted force becomes 455,000 pounds of force to the spine. In another instance, unprotected, 45 degrees from the body then the spine force is 2× the weight, the force is 2,000,000 pounds of force to the spine. While using the disclosed assembly, the actual force seen by the spine is 220,000 lbf. and the assembly transmuted force becomes 1,780,000 pounds of force to the spine. In another instance, unprotected, 90 degrees from the body then the spine force is 4× the weight of the item, the force is 4,000,000 pounds of force to the spine. While using the disclosed assembly, the actual force seen by the spine is 440,000 lbf. and the assembly transmuted force becomes 3,560,000 pounds of force to the spine.

Anatomic, Posture Conforming: The disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: the disclosed assembly conforms to the shapes of the thoracic kyphosis, and lumbar lordosis.

Spine Force Modulating—with variability of thickness of carbon fiber, and variable cutouts of hexagons, squares, circles, and others, was varied the strength, and flexibility of the frame which changes the ability to disperse forces and provide comfort.

Transmutation—The forces are transmuted from the vertebra, spine, spinal cord, and disc spaces and carried by the disclosed assembly.

Cervical Freedom—The disclosed assembly has an inherent cervical spine range-of-motion freedom which allows flexion and extension of the cervical spine, which serves to unload the stress seen on the neck.

Sacral Freedom—The disclosed assembly has an inherent sacral motion freedom which allows anterior and posterior tilting of the pelvis, which serves to unload the stress seen on the spine, allowing inherent pelvic freedom as another source of mitigating spine stresses.

Carrying In a Backpack: It was estimated for a regular person carrying 5,000 pounds per year in a backpack. When a person carries 5,000 pounds of weight per year in a backpack: unprotected, with a straight spine, the spine sees 3,500 pounds of force. While using the disclosed assembly, the spine sees 385 lbf., and 3,115 pounds of force is transmuted. In another instance, unprotected, when the person leans forward 10°, the spine sees 45,000 pounds of force. While using the disclosed assembly, the spine sees 4,950 lbf., and 40,050 pounds of force is transmuted. In another instance, unprotected, when the person leans forward 20°, the spine sees 60,000 pounds of force. While using the disclosed assembly, the spine sees 6,600 lbf., and 53,400 pounds of force is transmuted. In another instance, unprotected, when the person leans forward 40°, the spine sees 75,000 pounds of force. While using the disclosed assembly, the spine sees 8,250 lbf., and 66,750 pounds of force is transmuted.

Estimates for a regular person carrying 18,000 pounds per year in a backpack. Therefore, when a person carries 18,000 pounds of weight per year in a backpack: unprotected with a straight spine, the spine sees 126,000 pounds of force. While using the disclosed assembly, the spine sees 13,860 lbf., and 112,140 pounds of force is transmuted. In another instance, unprotected, when the person leans forward 10°, the spine sees 162,000 pounds of force. While using the disclosed assembly, the spine sees 17,820 lbf., and 144,180 pounds of force is transmuted. In another instance, unprotected, when the person leans forward 20°, the spine sees 216,000 pounds of force. While using the disclosed assembly, the spine sees 23,760 lbf., and 192,240 pounds of force is transmuted. In another instance, unprotected, when the person leans forward 40°, the spine sees 270,000 pounds of force. While using the disclosed assembly, the spine sees 29,720 lbf., and 240,300 pounds of force is transmuted When a person carries 1,000,000 pounds of weight per year in a backpack: In another instance, unprotected, with a straight spine, the spine usually sees 7,000,000 pounds of force. While using the disclosed assembly, the spine sees 770,000, and 6,230,000 pounds of force is transmuted. In another instance, unprotected, when the person leans forward 10°, the spine sees 8,500,000 pounds of force. While using the disclosed assembly, the spine sees 935,000 lbf., and 7,565,000 pounds of force is transmuted. In another instance, unprotected, when the person leans forward 20°, the spine sees 12,000,000 pounds of force. While using the disclosed assembly, the spine sees 1,320,000 lbf., and 10,680,000 pounds of force is transmuted. In another instance, unprotected, when the person leans forward 40°, the spine sees 15,000,000 pounds of force. While using the disclosed assembly, the spine sees 1,650,000 lbf., and 13,350,000 pounds of force is transmuted.

Anatomic, Posture Conforming: the disclosed assembly can improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study. Anatomic, Posture Conforming: The disclosed assembly conforms to the shapes of thoracic kyphosis, and lumbar lordosis. Spine Force Modulating— With variability of thickness of carbon fiber, and variable cutouts of hexagons, squares, circles, and others, we vary the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—The disclosed assembly has an inherent cervical spine range-of-motion freedom which allows flexion and extension of the cervical spine, which serves to unload the stress seen on the neck. Sacral Freedom—The disclosed assembly has an inherent sacral motion freedom which allows anterior and posterior tilting of the pelvis, which serves to unload the stress seen on the spine, allowing inherent pelvic freedom as another source of mitigating spine stresses.

For degenerative disc disease, biomechanical studies say that structural failures associated with intervertebral discs are annulus tears, disc prolapse, endplate damage, disc narrowing, radial bulging, and subsequent osteophyte formation in the vertebrae. Mechanically, intervertebral discs are found to be vulnerable to compression, flexion, axial rotation, and complex loading mechanisms through single impact, cyclical, and continuous loading. Chronic and repetitive loadings have a more damaging impact on the spine. Significant consequences include imbalance of metabolic enzymes and growth factors, alteration in stress profiles of intervertebral discs and a decrease in mechanical stiffness resulting in impaired biomechanics of the spine.

For degenerative disc disease the role of structure and functional changes of sensory nervous system in the induction and the maintenance of low back pain is being studied more and more. Studies suggest that intervertebral cell exhaustion and extracellular matrix degradation result in intervertebral structural damage. Neovascularization, innervation and inflammatory activation further deteriorate the microenvironment of the intervertebral disc. Nerve ingrowth into degenerated intravertebral disc amplifies the impacts of intervertebral disc derived nociceptive molecules on sensory endings. Under mechanical and pro-inflammatory stimulation, the pain-transmitting pathway exhibits a sensitized function state and ultimately leads to low back pain.

For degenerative disc diseases, the disclosed assembly having the inherent mechanical support, serves to absorb the spinal forces seen by the spine with intervertebral disc degeneration and identified as noted, allowing the suffering patient to experience less spine stress, and therefore less pain, and therefore the opportunity to resume more normal functionality such as walking, lifting, sitting and in activities of daily living.

Lessened spine stresses allow for less inflammation leading to a cooler annular tear interface. This is to say that the annular tear is present, however with less stress the tears present less inflammation, leading to less pain. Less inflammation also leads to a propensity for less sensory nervous system changes invoking painful neovascularization and deterioration of the microenvironment of the intervertebral disc. The disclosed assembly has an inherent sacral motion freedom which allows anterior and posterior tilting of the pelvis, which serves to unload the stress seen on the spine. Allowing inherent pelvic freedom is another source of mitigating spine stresses.

Anatomic, Posture Conforming: The disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of the thoracic kyphosis and lumbar lordosis. Spine Force Modulating—With variability of thickness of carbon fiber, and variable cutouts of hexagons, squares, circles and others, we vary the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—the disclosed assembly has an inherent cervical spine range-of-motion freedom which allows flexion and extension of the cervical spine, which serves to unload the stress seen on the neck. Sacral Freedom—disclosed assembly has an inherent sacral motion freedom which allows anterior and posterior tilting of the pelvis, which serves to unload the stress seen on the spine, allowing inherent pelvic freedom as another source of mitigating spine stresses.

For herniated disc disease in recent years various immunology, immunohistochemistry and molecular biology studies have shown that the herniated tissue is not an inert material, but rather it Is biologically very active with the capability of expressing a series of inflammatory mediators: cytokines such as interleukin-1, interleukin-6, interleukin-8 and tumor necrosis factor being the ones which stand out. The inflammation is not only induced by the chemical irritation of the bioactive substances released by the nucleus pulposus but also by an autoimmune response against itself. Thus, in addition to the mechanical factor, the biomechanical mediation plays an important role in the pathophysiology of sciatic pain and of radiculopathy.

For herniation of an intervertebral disc, the disclosed assembly having the inherent mechanical support, serves to absorb the spinal forces seen by the spine with a herniated disc and identified as noted, allowing the suffering patient to experience less spine stress, and therefore less pain, and therefore the opportunity to resume more normal functionality such as walking, lifting, sitting and activities of daily living. The disclosed assembly has an inherent sacral motion freedom which allows anterior and posterior tilting of the pelvis, which serves to unload the stress seen on the spine. Allowing inherent pelvic freedom as another source of mitigating spine stresses.

Anatomic, Posture Conforming: the disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of thoracic kyphosis, and lumbar lordosis. Spine Force Modulating—With variability of thickness of carbon fiber, and variable cutouts of hexagons, squares, circles, and others, we vary the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—disclosed assembly has an inherent cervical spine range-of-motion freedom which allows flexion and extension of the cervical spine, which serves to unload the stress seen on the neck. Sacral Freedom—disclosed assembly has an inherent sacral motion freedom which allows anterior and posterior tilting of the pelvis, which serves to unload the stress seen on the spine, allowing inherent pelvic freedom as another source of mitigating spine stresses.

For spinal stenosis, biomechanical studies, such as three-dimensional finite element models, three-dimensional kinematic measurement, cadaveric evaluation, and imaging assessment were applied to correlate lumbar biomechanics and lumbar spinal stenosis. The results show that the stresses significantly concentrate on the posterolateral part of the annulus fibrosus of disc, the posterior surface of vertebral body, the pedicle, the interarticularis and the facet joints. This trend is intensified by disc degeneration and lumbar backward extension. Furthermore, posterior element resection has a definite effect upon the biomechanical behavior of lumbar vertebrae.

For spinal stenosis, the disclosed assembly serves to support the spine and absorb the spinal forces seen by the spine and identified in its typical posterior and posterior lateral zones of the spine, allowing the suffering patient to experience less spine stress, and therefore less pain, and therefore the opportunity to resume more normal functionality such as walking, lifting, sitting activities of daily living.

Our disclosed assembly has an inherent sacral motion and pelvic freedom which allows either an anterior or a posterior pelvic tilt, which serves to unload the stress seen on the posterior aspect of the spine. This is no different than the patient tilting forward as seen in the shopping cart sign. In the shopping cart sign scenario, a patient tilts forward and unloads the posterior identified stressors.

Anatomic, Posture Conforming: The disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of thoracic kyphosis, and lumbar lordosis. Spine Force Modulating—With variability of thickness of carbon fiber, and variable cutouts of hexagons, squares, circles, and others, was varied the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—the disclosed assembly has an inherent cervical spine range-of-motion freedom which allows flexion and extension of the cervical spine, which serves to unload the stress seen on the neck. Sacral Freedom—the disclosed assembly has an inherent sacral motion freedom which allows anterior and posterior tilting of the pelvis, which serves to unload the stress seen on the spine, allowing inherent pelvic freedom as another source of mitigating spine stresses.

For spondylolisthesis, studies show that with mechanical equations it has been established, that the pars interarticularis and the ligaments together resist the tensile and shear force, the bending moment if the pars interarticularis is uncracked. When there is further stress the pars interarticularis reaches its strength and cracking of the pars interarticularis occurs, leading to a condition called spondylolysis. When the cracked pars interarticularis also known as spondylolysis is no longer capable of sustaining tension, then tensile forces are transferred to the ligament. If the tensile stress in the ligament reaches its strength and the ligament breaks, the pars interarticularis cracks through, and the vertebra slips and a condition called spondylolisthesis develops. Furthermore, as the so-called pelvic incidence which measures the sacral slope tilts forward, anteriorly, then the lumbar spine compensates with more lordosis, and the thoracic spine compensates with more thoracic kyphosis. This necessarily generates increase magnitude of spine forces in the thoracic kyphosis and lumbar lordosis.

For spondylolisthesis, the disclosed assembly with its inherent mechanical support, serves to absorb the spinal forces seen by the spine spondylolisthesis and identified as noted, allowing the suffering patient to experience less spine stress, and therefore less pain, and therefore the opportunity to resume more normal functionality such as walking, lifting, sitting and in general living. The disclosed assembly further subsumes thoracic and lumbar excess forces seen with advancing spondylolisthesis.

Lessened spine stresses allow for less inflammation of the pars interarticularis in spondylolysis and the vertebra slippage of spondylolisthesis leading to cooler pars interarticularis and vertebra slippage interfaces. This is to say that the fracture of pars interarticularis in spondylolysis is present however with less stresses the pars interarticularis in spondylolysis present less inflammation, leading to less pain. This is to furthermore say that the vertebra slippage of spondylolisthesis is present however with less stresses the vertebra slippage of spondylolisthesis presents less inflammation, leading to less pain. Furthermore, with the inherent anatomic shape in the thoracic kyphosis, and the lumbar lordosis of the disclosed assembly, then the excess stress seen with enhanced lumbar lordosis and enhanced thoracic kyphosis are mitigated.

Anatomic, Posture Conforming: The disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of thoracic kyphosis, and lumbar lordosis. Spine Force Modulating—With variability of thickness of carbon fiber, and variable cutouts of hexagons, squares, circles, and others, was varied the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—the disclosed assembly has an inherent cervical spine range-of-motion freedom which allows flexion and extension of the cervical spine, which serves to unload the stress seen on the neck. Sacral Freedom—the disclosed assembly has an inherent sacral motion freedom which allows anterior and posterior tilting of the pelvis, which serves to unload the stress seen on the spine, allowing inherent pelvic freedom as another source of mitigating spine stresses. The importance of pelvic posture has emerged as a consequential force generator or mitigator.

For scoliosis, the anatomic nature of the disclosed assembly with attention to normal thoracic and lumbar spine curvature recreation lead to better posture, corrected slumping, less bending, repositioning of the spatial arrangement of trunk muscles and the anti-gravitational effect. The strength of the carbon fiber allows for enhanced de-rotation of the torso and provides a fulcrum of support for corrections and over corrections. Lateral pads may further support the spine with corrections. Right and left side specific adjustments of the straps allow for correction of the typical one side being higher than the other.

Anatomic, Posture Conforming: the disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of the thoracic kyphosis, and lumbar lordosis. Spine Force Modulating—With variability of thickness of carbon fiber, and variable cutouts of hexagons, squares, circles, and others, we vary the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—disclosed assembly has an inherent cervical spine range-of-motion freedom which allows flexion and extension of the cervical spine, which serves to unload the stress seen on the neck. Sacral Freedom disclosed assembly has an inherent sacral motion freedom which allows anterior and posterior tilting of the pelvis, which serves to unload the stress seen on the spine, allowing inherent pelvic freedom as another source of mitigating spine stresses.

One in five men and one in three women over the age of fifty will suffer an osteoporotic fracture due to weakened bones as stated by the International Osteoporosis Foundation data. For osteoporosis, the disclosed assembly for the back diminishes the forces seen by the spine by 89%, allows for postural straightening of the spine, diminishing the chances of degeneration of the spine, and the chances of a repeat fracture.

25% of osteoporotic hip fractures occur in men, and the 1-year mortality in men is 20% higher compared with women. It has been estimated that in the future that compared with rates of osteoporotic fracture in 1990, by 2050, the incidence of osteoporotic hip fractures will increase 240% in women and 310% in men.

When kyphoplasty cement augmentation surgery is performed, there are conflicting data regarding the incidence of subsequent adjacent fracture, ranging anywhere from 3 to 29%. It is known that a patient with one fracture is 5× likely to have a second fracture. A patient with two fractures is 12× likely to have a third fracture. A patient with three fractures is 75× likely to have a fourth fracture.

Anatomic, Posture Conforming: The disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of thoracic kyphosis, and lumbar lordosis. Spine Force Modulating—With variability of thickness of carbon fiber, and variable cutouts of hexagons, squares, circles, and others, we vary the strength, and flexibility of the disclosed assembly which changes the ability to disperse forces and provide comfort. Transmutation—The forces are transmuted from the vertebra, spine, spinal cord and disc spaces and carried by the disclosed assembly. Cervical Freedom—disclosed assembly has an inherent cervical spine range-of-motion freedom which allows flexion and extension of the cervical spine, which serves to unload the stress seen on the neck. Sacral Freedom—disclosed assembly has an inherent sacral motion freedom which allows anterior and posterior tilting of the pelvis, which serves to unload the stress seen on the spine, allowing inherent pelvic freedom as another source of mitigating spine stresses.

Propensity for fracture of normal bones and spine forces with disclosed assembly. Vertebral bone can withstand average stress of from 100 to 250 MPa before fracture. The backpack study showed that a 50-lb backpack exerts about 1.21 MPa of stress in the neutral position and 32.2 MPa in the forward flexion position. A 100-lb backpack exerts two values: 2.42 MPa in the neutral position and 64.4 MPa in the forward flexion position. While the values for a neutral spine are safe concerning the fracture threshold, under forward flexion, backpacks of 50 and 100 lbs. exert 32.2% and 64.4%, respectively, of the minimum stress for bone failure. These values are for the static/stationary case and may be magnified under dynamic conditions.

The disclosed assembly can also be adapted for age adjusted thoracic and lumbar curvatures. While no two spines are altogether alike, some people have spine degeneration and herniations in their twenties, others can maintain supple spines into their nineties. While spine degeneration occurs differently in all people. With aging anterior tilting of the head and plumbline of the body moves the body anterior to the femoral head further unbalancing the spine leading to the generation of unbalanced thoracic and lumbar spine forces. The thoracic kyphosis is increased yielding a larger curve. The lumbar lordosis is increased leading to a larger curve. The body compensates by flexing the hip joints leading to a shorter person and hip stiffness. The knee joints similarly flex, leading to a shorter person and knee stiffness.

The disclosed assembly matches the alignment of the spine especially with the thoracic kyphosis and lumbar lordosis. In the study was modeled a younger spine with 30 degrees of thoracic kyphosis, and 30 degrees of lumbar lordosis in this instance. However, the numbers change as the person gets older, as in other instances and will be reflected in other iterations. While the original design modulates 30 degrees of thoracic kyphosis, and 30 degrees of lumbar lordosis as a model for younger spines, older spines are modelled according to the modelling of the aging spine presented before which can be 40 degrees of thoracic kyphosis and 40 degrees of lumbar lordosis, or 45 degrees of thoracic kyphosis and 45 degrees of lumbar lordosis, or 50 degrees of thoracic kyphosis and 50 degrees of lumbar lordosis as examples. The disclosed assembly can be made for custom sizes to accommodate the aging patients.

The disclosed assembly leads to subsuming the excess forces seen especially in the thoracic spine and the lumbar spine, this leads to less spine forces, less stress less unbalancing and therefore less pain. Less inflammation also leads to a propensity for less sensory nervous system changes invoking painful neovascularization and deterioration of the microenvironment of the intervertebral disc. Furthermore, with the inherent anatomic shape in the thoracic kyphosis, and the lumbar lordosis of the disclosed assembly, then the excess stress seen with enhanced lumbar lordosis and enhanced thoracic kyphosis are mitigated.

Anatomic, Posture Conforming: The disclosed assembly improves the posture of the person by improvement of the alignment of the person by enhancing the person's posture: standing erect (X-plane correction), standing taller (Y-plane correction), and opening the chest, embracing proper thoracic kyphosis, proper lumbar lordosis, tightening waist circumference and allowing for pelvic tilting (Z-plane corrections) as augmented by the disclosed assembly. Further measurable force reductions on the spine are noted in accordance with the text neck study, the belly fat study, and the backpack study.

Anatomic, Posture Conforming: The disclosed assembly conforms to the shapes of thoracic kyphosis, and lumbar lordosis. Spine Force Modulating—With variability of thickness of carbon fiber, and variable cutouts of hexagons, squares, circles, and others, was varied the strength, and flexibility of the disclosed assembly which changes the ability to disperse forces and provide comfort. Transmutation—The forces are transmuted from the vertebra, spine, spinal cord, and disc spaces and carried by the disclosed assembly. Cervical Freedom—disclosed assembly has an inherent cervical spine range-of-motion freedom which allows flexion and extension of the cervical spine, which serves to unload the stress seen on the neck. Sacral Freedom—disclosed assembly has an inherent sacral motion freedom which allows anterior and posterior tilting of the pelvis, which serves to unload the stress seen on the spine, allowing inherent pelvic freedom as another source of mitigating spine stresses. Additional Postural Sources of Efficiency.

Cervical Lordosis is the natural C-shape of the neck which is belly shaped. There are 7 cervical vertebrae called the neck. The cervical spine is the neck. Normal cervical lordosis is 30 to 40 degrees. Proper alignment of the cervical spine is very sensitive for forces placed onto the spine. In the study "Assessment of stresses in the cervical spine caused by posture and position of the head" it was found that the head weighs 10 to 12 pounds to the neck in a neutral position, when flexed forward at 15 degrees, the head exerts 27 pounds of force, when flexed forward at 30 degrees, the head exerts 40 pounds of force, when flexed forward at 45 degrees, the head exerts 49 pounds of force, and when flexed forward at 60 degrees, the head exerts 60 pounds of force. When a person straightens their head, which is easier to do with the disclosed assembly, then there is reduced spine forces.

Thoracic Kyphosis is the natural reverse C-shape of the mid-back spine which is reverse belly shaped. There are 12 thoracic vertebrae called the midback. The thoracic spine is the mid back. Normal thoracic lordosis is 20 to 40 degrees. Less than 20 degrees of kyphosis=hypokyphosis, while greater than 50 degrees is called a "kyphosis" problem. Similarly, the alignment of the thoracic spine is very sensitive for forces placed onto the spine. For example: according to our study "Backpack Forces on the spine," When a regular person carries 1 pound in a backpack: with a straight spine, the spine sees 7 pounds of force; when the person leans forward 10°, the spine sees 9 pounds of force; when the person leans forward 20°, the spine sees 12 pounds of force; and when the person leans forward 40°, the spine sees 15 pounds of force. The disclosed assembly subsumes 89% of the spine force in each case.

Furthermore, as described before in the study "Breast Forces on the spine," the magnitude of the forces generated by the breast to the thoracic spine ranged between 9 pounds of force for underwire size 30 to 110 pounds of force for underwire size 60, in the erect neutral spine position. When the person tilts over 20°, then the forces are multiplied 1.4×. The disclosed assembly subsumes 89% of the spine force in each case.

Lumbar Lordosis is the natural C-shape of the lower back which has a belly shaped curvature. The lumbar spine is the lower back. There are 5 lumbar vertebrae called the back. Normal lumbar lordosis is typically between 20 to 40 degrees. When the angle of the lumbar curve is large, often called a sway back, it can cause a lot of problems—including misalignment leading to pain. When the angle of the lumbar spine is too low a condition called flat back exists and may be associated with disc degeneration or herniated discs, causing pain.

Similarly, the alignment of the lumbar spine is very sensitive for forces placed onto the spine. For example: according to our study Belly Fat Forces on the Spine: Finite Element Analyses of Belly Fat Forces by Waist Circumference, in women: The average magnitude of forces generated by abdominal fat to the lumbar spine ranged between 5 to 170 pounds of force in our measurements. The average woman with a: 25 inches waist circumference exerts 5 pounds of force to the spine, 30 inches waist circumference exerts 22 pounds of force to the spine, 35 inches waist circumference exerts 41 pounds of force to the spine, 40 inches waist circumference exerts 62 pounds of force to the spine, 45 inches waist circumference exerts 77 pounds of force to the spine, 50 inches waist circumference exerts 95 pounds of force to the spine, 55 inches waist circumference exerts 114 pounds of force to the spine, 60 inches waist circumference exerts 132 pounds of force to the spine, 65 inches waist circumference exerts 150 pounds of force to the spine, and 70 inches waist circumference exerts 170 pounds of force to the spine. Black women had significantly greater belly fat forces than White ($P<0.004$) and Hispanic women ($P<0.02$), while there was no significant difference between White and Hispanic women ($P<0.9$). The disclosed assembly subsumes 89% of the spine force in each case.

Similarly, in men, the average magnitude of forces generated by abdominal fat to the lumbar spine ranged between 5 to 120 pounds of force in our measurements. The average man with a: 25 inches waist circumference exerts 3 pounds of force to the spine, 30 inches waist circumference exerts 12 pounds of force to the spine, 35 inches waist circumference exerts 25 pounds of force to the spine, 40 inches waist circumference exerts 39 pounds of force to the spine, 45 inches waist circumference exerts 51 pounds of force to the spine, 50 inches waist circumference exerts 65 pounds of force to the spine, 55 inches waist circumference exerts 79 pounds of force to the spine, 60 inches waist circumference exerts 93 pounds of force to the spine, 65 inches waist circumference exerts 107 pounds of force to the spine, and 70 inches waist circumference exerts 120 pounds of force to the spine. Black men had significantly greater belly fat forces than White ($P<0.009$) and Hispanic men ($P<0.007$), while there was no significant difference between White and Hispanic men (P<0.17). The disclosed assembly subsumes 89% of the spine force in each case.

The sacrum and the coccyx which make up your tailbone. The sacral spine is the sacrum, and it is a reverse belly shape similar to the thoracic spine. The coccyx the lowest part of the spine turns forward into the pelvis. Core strengthening as a source of force reduction: these spinal forces highlight the importance of the inner core (iliopsoas muscle), and outer core (abdominal, back and buttock muscles) in carrying loads on the spine. Similarly, the quadriceps, hamstrings and gastrocnemius soleus muscles provide a source of shock absorption of spine forces.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A spine force modulating assembly comprising:
    a frame of a length proportional to a distance between a third thoracic spine bone and a first sacral spine bone of a spine of a wearer of the spine force modulating assembly, wherein the frame is of a "S" shape and configured to support a spine portion between the third thoracic spine bone and the first sacral spine bone, the shape of the frame conforms to thoracic and lumbar spine that matches natural reverse c-shape alignment of the thoracic spine with kyphosis and natural c-shape of the lumbar spine in lordosis, wherein said spine force modulating assembly is for dispersing, transmitting, transmuting, and subsuming spine forces while supporting a human spine, and wherein the spine force modulating assembly improves an alignment of a person by enhancing the person's posture, standing erect (X-plane correction), standing taller (Y-plane correction), and opening the chest, embracing proper thoracic kyphosis, proper lumbar lordosis, tightening waist circumference and pelvic tilting (Z-plane corrections), the spine force modulating assembly increases efficiency of load carrying capability of the person while diminishing stresses seen by the spine.

2. The spine force modulating assembly according to claim 1, wherein the frame has an upper portion and a lower portion, the upper portion has an upper end, the lower portion has a lower end, wherein the spine force modulating assembly further comprises:
    a pair of shoulder straps that extends between near the upper end of the frame and respective sides of the lower portion of the frame, and
    a lumbar level waist strap coupled to both sides of the frame at the lower portion thereof and configured to compress lower back and abdomen, the lumber level waist strap configured such that when strapped, the person's lower back conforms to the lumbar curvature built into the frame.

3. The spine force modulating assembly according to claim 2, wherein the frame is of a width covering a width of a vertebral body and extends laterally to cover the width of the vertebral body and erector spinae muscle—the iliocostalis, the longissimus, the spinalis, rhomboid major and minor.

4. The spine force modulating assembly according to claim 1, wherein the frame is made from carbon fibers, wherein the frame is designed using numerical analyses using finite element mathematics and further enhanced with topology optimization subroutine resulting in balancing of stiffness, flexibility, and strength.

5. The spine force modulating assembly according to claim 4, wherein the carbon fibers are oriented at about 45 degrees from a longitudinal axis.

6. The spine force modulating assembly according to claim 1, wherein the frame has a plurality of holes dispersed throughout an area of the frame.

7. The spine force modulating assembly according to claim 6, wherein the plurality of holes are hexagonal shaped.

8. The spine force modulating assembly according to claim 6, wherein the frame does not support cervical bones in order to allow freedom of range-of-motion of neck.

9. The spine force modulating assembly according to claim 8, wherein the frame does not support second to fifth sacral bones and pelvis to allow freedom of range-of motion of the pelvis.

10. A method for dispersing, transmitting, transmuting, and subsuming spine forces while supporting a human spine, the spine forces relate to neck posture, breast forces, backpack forces, belly fat forces and lifting forces, the method comprises:
    providing a dynamic, anatomic, postural, and conforming spine force modulating assembly, the spine force modulating assembly improves an alignment of a person by enhancing the person's posture: standing erect (X-plane correction), standing taller (Y-plane correction), and opening the chest, embracing proper thoracic kyphosis, proper lumbar lordosis, tightening waist circumference and pelvic tilting (Z-plane corrections), the spine force modulating assembly increases efficiency of load carrying capability of the person while diminishing stresses seen by the spine, wherein the spine force modulating assembly:
        comprises a frame of a length proportional to a distance between a third thoracic spine bone and a first sacral spine bone of a spine of a wearer of the spine force modulating assembly, wherein the frame is of a "S" shape and configured to support a spine portion between the third thoracic spine bone and the first sacral spine bone, the shape of the frame conforms to thoracic and lumbar spine that matches natural reverse c-shape alignment of the thoracic spine with kyphosis and natural c-shape of the lumbar spine in lordosis; and
    wearing the spine force modulating assembly by the person, wherein the frame of the spine force modulating assembly spatially extends between the third thoracic spine bone and the first sacral spine bone of a spine, wherein the frame does not support cervical bones in order to allow freedom of range-of-motion of neck, and wherein the frame does not support second to fifth sacral bones and pelvis to allow freedom of range-of motion of the pelvis.

11. The method according to claim 10, wherein the frame has an upper portion and a lower portion, the upper portion has an upper end the lower portion has a lower end, wherein the spine force modulating assembly further comprises:
    a pair of shoulder straps that extends between near the upper end of the frame and respective sides of the lower portion of the frame, and a lumbar level waist strap coupled to both sides of the frame at the lower portion thereof and configured to compress lower back and abdomen.

12. The method according to claim 10, wherein the frame is made from carbon fibers.

13. The method according to claim 12, wherein the carbon fibers are oriented at about 45 degrees from a longitudinal axis.

14. The method of claim 10, wherein wearing the spine force modulating assembly help correcting degenerative disc disease, herniated disc disease, spinal stenosis, spondylolisthesis, spondylolysis, scoliosis, osteoporosis conditions, manifestations of aging of a spine, and intervertebral disc degeneration.

* * * * *